US011495327B2

(12) United States Patent
El-Baz et al.

(10) Patent No.: US 11,495,327 B2
(45) Date of Patent: Nov. 8, 2022

(54) COMPUTER-AIDED DIAGNOSTIC SYSTEM FOR EARLY DIAGNOSIS OF PROSTATE CANCER

(71) Applicant: University of Louisville Research Foundation, Inc., Louisville, KY (US)

(72) Inventors: Ayman S. El-Baz, Louisville, KY (US); Ahmed Shalaby, Louisville, KY (US); Fahmi Khalifa, Louisville, KY (US); Islam Abdelmaksoud, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1157 days.

(21) Appl. No.: 16/030,296

(22) Filed: Jul. 9, 2018

(65) Prior Publication Data

US 2020/0012761 A1  Jan. 9, 2020
US 2020/0285714 A9  Sep. 10, 2020

Related U.S. Application Data

(60) Provisional application No. 62/529,772, filed on Jul. 7, 2017.

(51) Int. Cl.
G16B 40/00 (2019.01)
G16B 5/00 (2019.01)

(52) U.S. Cl.
CPC ............. *G16B 40/00* (2019.02); *G16B 5/00* (2019.02)

(58) Field of Classification Search
None
See application file for complete search history.

(56) References Cited

PUBLICATIONS

Reda I et al., "A new NMF-autoencoder based CAD system for early diagnosis of prostate cancer," Jun. 2016 IEEE 13th International Symposium on Biomedical Imaging (ISBI), 2016, pp. 1237-1240.*
Le MH, Chen J, Wang L, Wang Z, Liu W, Cheng KT, Yang X. Automated diagnosis of prostate cancer in multi-parametric MRI based on multimodal convolutional neural networks. Phys Med Biol. Jul. 24, 2017;62(16):6497-6514.*
Wikipedia, "Autoencoder," (https://en.wikipedia.org/wiki/Autoencoder), 9 pages, downloaded Feb. 11, 2022.*
Wikipedia, "Softmax function," (https://en.wikipedia.org/wiki/Softmax_function), 8 pages, downloaded Feb. 11, 2022.*
Brownlee, Jason. "How to develop voting ensembles with python," Machine Learning Mastery, downloaded Feb. 11, 2022 from (https://machinelearningmastery.com/voting-ensembles-with-python/), 18 pages, (2020).*
Siegel R L, Miller K D and Jemal A. Cancer statistics, 2016. CA Cancer J. Clin 2016; (66(1): 7-30.

Ferlay J, Shin H R, Bray F et al. GLOBOCAN 2008, Cancer incidence and mortality worldwide: IARC CancerBase No. 10. Lyon, France: International Agency for Research on Cancer 2010; 2.
Mistry K and Cable G. Meta analysis of prostate-specific antigen and digital rectal examination as screening tests for prostate carcinoma. J Am Board Fam Pract 2003; 16(2): 95-101.
Dijkstra S, Mulders P and Schalken J. Clinical use of novel urine and blood based prostate cancer biomarkers: a review. Clin Biochem 2014; 47(10-11): 889-896.
Davis M, Sofer M, Kim SS et al. The procedure of transrectal ultrasound guided biopsy of the prostate: a survey of patient preparation and biopsy technique. J Urol 2002;167(2): 566-570.
Hricak H, Choyke PL, Eberhardt S C et al. Imaging prostate cancer: a multidisciplinary perspective 1. Radiology 2007 243(1): 28-53.
Applewhite JC, Matlaga B, Mccullough D et al. Transrectal ultrasound and biopsy in the early diagnosis of prostate cancer. Cancer Control 2000; 8(2): 141-150.
Tan C H, Wang J and Kundra V. Diffusion weighted imaging in prostate cancer. Eur Radiol 2011; 21(3): 593-603.
Tamada T, Sone T, Jo Y et al. Diffusion-weighted MRI and its role in prostate cancer. NMR Biomed 2014; 27(1) 25-38.
Viswanath S E, Bloch N B, Chappelow J C et al. Central gland and peripheral zone prostate tumors have significantly different quantitative imaging signatures on 3 tesla endoctoral, in vivo T2 weighted M R imagery. J Magn Reson Imaging 2012; 36(1): 213-224.
Hambrock T, Vos P C, Hulsbergen-V D KAA CA et al. Prostate cancer: computer-aided diagnosis with multiparametric 3-T MR imaging effect on observer performance. Radiology 2013; 266(2): 521-530.
Litjens G, Debats O, Barentsz J et al. Computer-aided detection of prostate cancer in MRI. IEEE Trans Med Imaging 2014; 33(5): 1083-1092.
Kwak J T, Xu S, Wood B J et al. Automated prostate cancer detection using T2-weighted and high-b-value diffusion-weighted magnetic resonance imaging. Med Phys 2015; 42(5): 2368-2378.
Peng Y, Jiang Y, Yang C et al. Quantitative analysis of multiparametric prostate M R images: differentiation between prostate cancer and normal tissue and correlation with gleason score—a computer-aided diagnosis development study. Radiology 2013: 267(3): 787-796.
Boesen L, Chabanova E, Logager V et al. Apparent diffusion coefficient ratio correlates significantly with prostate cancer gleason score at final pathology. J Magn Reson Imaging 2015; 42(2): 446-453.

(Continued)

*Primary Examiner* — G Steven Vanni
(74) *Attorney, Agent, or Firm* — Dentons Bingham Greenebaum LLP; Brian W. Chellgren

(57) ABSTRACT

Systems and methods for diagnosing prostate cancer. Image sets (e.g., MRI collected at one or more b-values) and biological values (e.g., prostate specific antigen (PSA)) have features extracted and integrated to produce a diagnosis of prostate cancer. The image sets are analyzed primarily in three steps: (1) segmentation, (2) feature extraction, smoothing, and normalization, and (3) classification. The biological values are analyzed primarily in two steps: (1) feature extraction and (2) classification. Each analysis results in diagnostic probabilities, which are then combined to pass through an additional classification stage. The end result is a more accurate diagnosis of prostate cancer.

15 Claims, 12 Drawing Sheets

(56) References Cited

PUBLICATIONS

Mcclure P, Khalifa F, Soliman A et al. A novel NMF guided level-set for DWI prostate segmentation. J Comput Sci Syst Biol 2014; 7(6): 209-216.

Le Bihan D. Apparent diffusion coefficient beyond: what diffusion MR imaging can tell us about tissue structure. Radiology 2013; 268(2): 318-322.

Bengio Y, Lamblin P, Popovici D et al. Greedy layer-wise training of deep networks. In Advances in neural information processing systems. Vancouver, BC, Canada, Dec. 4-7, 2006, pp. 153-160.

Han J, Zhang D, Wen S et al. Two-stage learning to predict human eye fixations via SDAEs. IEEE Trans Cybern 2016; 46(2): 487-498.

Boureau Y I, Cun Y L et al. Sparse feature learning for deep belief networks. In Advances in neural information processing systems. Vancouver, BC, Canada, Dec. 3-6, 2007, pp. 1185-1192.

Hosseni-Asl E, Zurada J M and Nasraoui O. Deep learning of part-based representation of data using sparse autoencoders with nonnegativity constraints. IEEE Trans Pattern Anal Mach Intell 2013; 35(8): 1798-1828.

Bengio Y, Courville A and Vincent P. Representation learning: A review and new perspectives. IEEE Trans Pattern Anal Mach Intell 2013; 35(8): 1798-1828.

Yan K, Li C, Wang X et al. Comprehensive autoencoder for prostate recognition on MR images. In IEEE international symposium on biomedical imaging. Prague, Czech Republic, Apr. 13-16, 2016: IEEE, pp. 1190-1194.

Rota Bulo S and Kontscheider P. Neural decision forests for semantic image labeling. In IEEE conference on computer vision and pattern recognition. Columbus, Ohio, USA, Jun. 24-27, 2014, pp. 81-88.

Tsehay Y KM Lay N S, Roth H R et al. Convolutional neural network based deep-learning architecture for prostate cancer detection on multiparametric magnetic resonance images. In SPIE medical imaging. Orlando, Fla., USA, Feb. 11-16, 2017, pp. 1013405-1013405.

Le M H, Chen J, Wang L et al. Automated diagnosis of prostate cancer in multi-parametric MRI based on multimodal convolutional neural networks. Phys. Med Biol 2017: 62(16): 6497-6514.

Clark T, Wong A, Haider M A et al. Fully deep convolutional neural networks for segmentation of the prostate gland in diffusion-weighted MR images. In International conference image analysis and recognition. Montreal, Canada, Jul. 5-7, 2017: Springer, pp. 97-104.

Chung A G, Shafiee M J, Kumar D et al. Discovery radiomics for multi-parametric MRI prostate cancer detection. arXiv preprint 2015; arXiv: 1509.00111.

Liu S, Zheng H, Feng Y et al. Prostate cancer diagnosis using deep learning with 3D multiparametric MRI. arXiv preprint 2017; arXiv: 1703.04078.

Hall M et al. The WEKA data mining sofware: an update. SIGKDD Explor Newsl 2009; 11(1): 10-18.

Skalska H and Freylich V. Web-bootstrap estimate of area under ROC curve. Austrian J Stat 2016; 35(2-3): 325-330.

\* cited by examiner

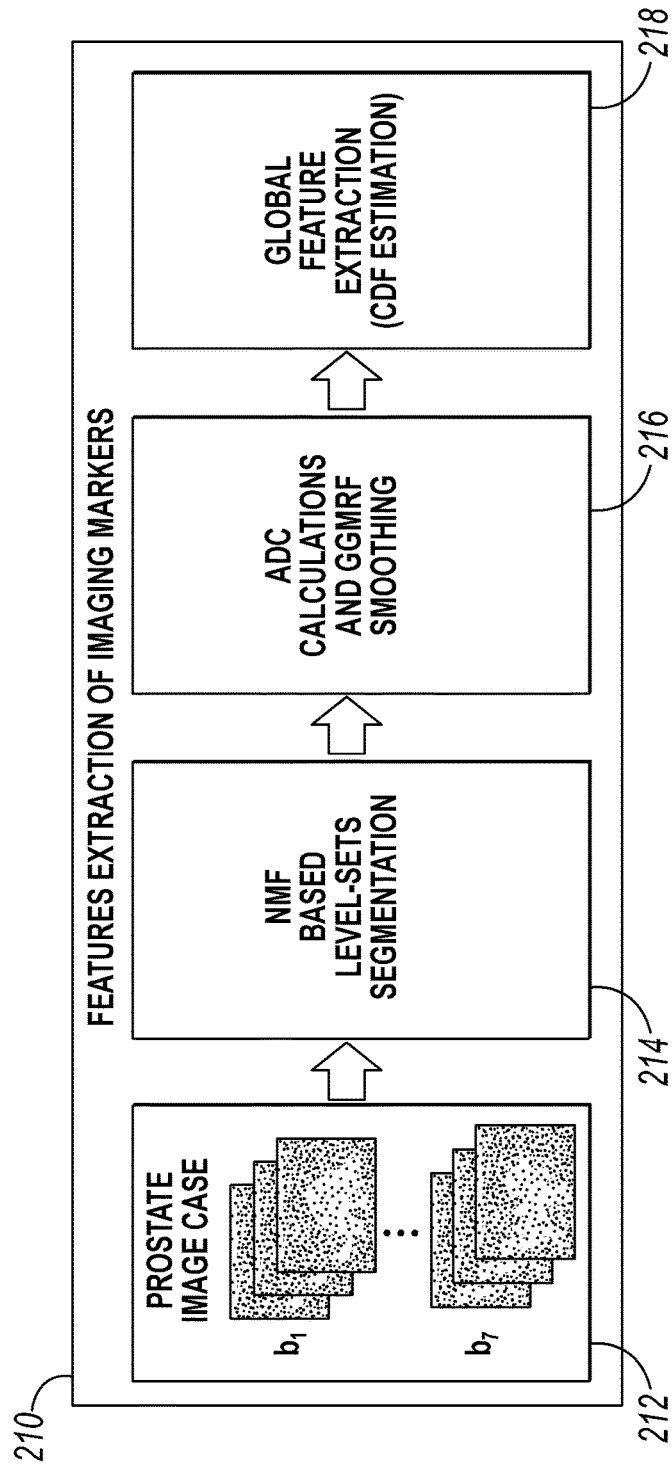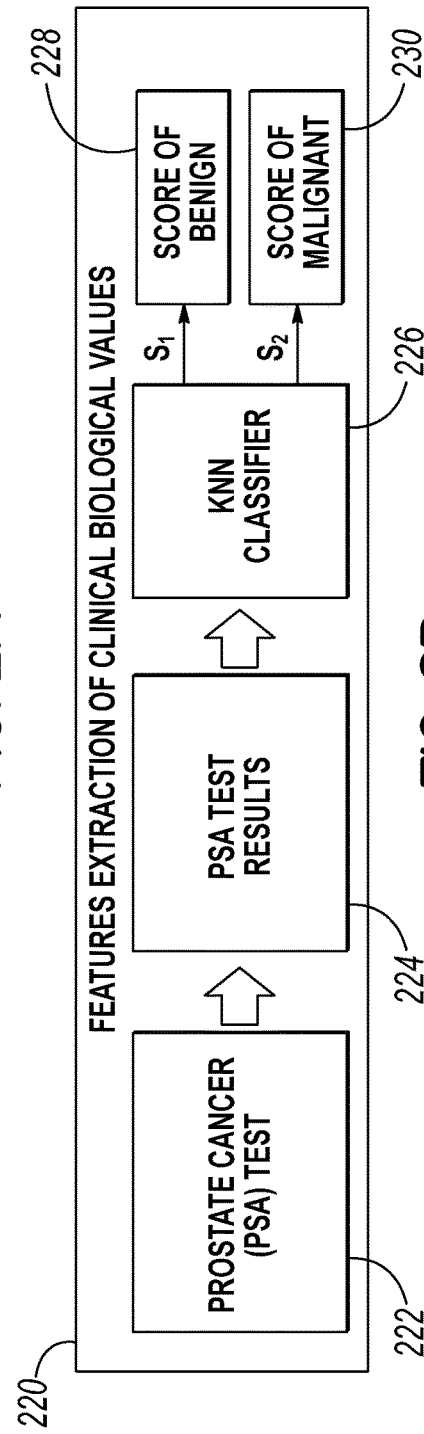
FIG. 2A
FIG. 2B

COMPUTER-AIDED DIAGNOSTIC SYSTEM FOR EARLY DIAGNOSIS OF PROSTATE CANCER

CROSS-REFERENCE TO RELATED APPLICATIONS

This application claims the benefit of and priority to U.S. Provisional Application No. 62/529,772 entitled COMPUTER-AIDED DIAGNOSTIC SYSTEM FOR EARLY DIAGNOSIS OF PROSTATE CANCER, filed Jul. 7, 2017, which is expressly incorporated by reference herein in its entirety.

FIELD OF THE INVENTION

This disclosure generally relates to computer analysis of medical image data and clinical data, and in particular to the analysis of medical images of the prostate and biological values that combined lead to a diagnosis related to prostate cancer based.

BACKGROUND OF THE INVENTION

Prostate cancer is one of the most frequent cancers identified among the male population in the United States, and accounts for the highest mortality rate due to cancer second only to lung cancer. According to statistics published by the American Cancer Society in 2016, around 180,890 new patients were diagnosed and around 26,120 patients passed away due to prostate cancer [1]. The incidence of prostate cancer increases as age progresses. By 2030, it is estimated there will be up to 1,700,000 prostate cancer incidences worldwide, and the related number of annual deaths will be around 500,000 [2]. Fortunately, the sooner prostate cancer is detected, the more likely it is to be treated successfully, minimizing the mortality rate.

Current screening techniques for prostate cancer include digital rectal examination (DRE) [3], prostate specific antigen (PSA) blood test [4], and needle biopsy [5]. Each of these techniques has their own shortcomings. In the DRE test, a doctor examines the prostate manually to identify anomalies in volume or hardness. The cost of DRE is relatively low, but DRE is highly invasive. Some peripheral-zone tumors can be identified using the DRE. However, most of the central-zone and transitional-zone tumors, as well as tumors too small to be palpated, cannot be detected through DRE. As a result, the positive predictive value, sensitivity, and specificity of the DRE are low [3]. The prevailing prostate examination measures the PSA enzyme concentration in the blood. A PSA level higher than 4 ng/mL (nanograms per milliliter) indicates a likelihood of prostate cancer. However, the elevated levels may also be due to other reasons, such as prostatitis or hyperplasia. In general, the positive predictive value, sensitivity, and specificity of the PSA screening are better than the DRE test [3]. However, both DRE and PSA are merely indicators of prostate cancer and are not conclusive diagnosis techniques.

If either the DRE or PSA test raises suspicion, patients may undergo further testing, such as needle biopsy, to confirm the existence or non-existence of the cancer. Transrectal ultrasound (TRUS)-guided biopsy acquires small tissue specimens from the prostate gland for evaluation by a pathologist. The Gleason grading system is the standard method used by pathologists for visual assessment of acquired specimens. The Gleason grading system is based on evaluating the two most predominant tumor patterns in the acquired specimen. To use this system, the pathologist evaluates each pattern on a scale from 1 to 5, where κ represents the most aggressive tumor. The Gleason score is the result of summing the scores of these two patterns. A score of 6 or more indicates the presence of prostate cancer. However, there is a possibility of missing a cancer tumor due to the small number of biopsy specimens, random nature of sampling, and poor resolution of TRUS. MRI/US-guided biopsy has been demonstrated to perform better than TRUS-guided biopsy. Even though biopsy is the most precise technique for detecting cancer, it is highly invasive, expensive, and a painful tool for detecting prostate cancer and determining its aggressiveness. Because of these shortcomings, accurate, sensitive, specific, and non-invasive diagnostic techniques are in a high demand.

Today's computer-aided diagnostic (CAD) systems analyze images from various modalities, such as ultrasound and MRI, to detect and localize prostate cancer and evaluate its size and extent. In clinical applications, each of these modalities has pros and cons. The most prevalent prostate imaging modality is TRUS as it is used to guide the needle biopsy and estimate the prostate volume [6]. In comparison to other imaging modalities, TRUS is portable, inexpensive, and generates real-time images. The negative aspects of TRUS imagery are low contrast, small signal-to-noise ratio, the existence of speckles, and shadow artifacts [7]. The interpretation of TRUS images may also be affected by the subjective nature of the examination and the experience of the clinician. Therefore, it is hard to precisely detect tumors and/or identify the cancer stage using TRUS images.

Various MRI modalities have been used in CAD systems for prostate cancer diagnosis. Diffusion-weighted magnetic resonance imaging (DW-MRI) is the most recent MRI modality for diagnosing prostate cancer. DW-MRI employs the diffusion of water molecules to indirectly identify cellularity of tissues. Cancerous prostate regions are typically characterized by increased cell densities, which result in more constrained diffusion as compared to healthy tissues. Even though the contrast of DW-MR images is not as good as the contrast of dynamic contrast enhanced MRI (DCE-MRI), the acquisition time of DW-MRI data is much shorter, and does not involve the use of contrast agents [8,9]. In general, using DW-MRI for diagnosing prostate cancer results in higher accuracy than using DCE-MRI or T2-weighted MRI [10].

Viswanath et al. [11] introduced a CAD system for detecting prostate cancer in both the central gland (CG) and the peripheral zone (PZ) from T2-weighted MRI. In one such system, 110 textural features were extracted. Then a feature selection approach was performed to choose the minimum number of features with the best accuracy, in terms of the area under the curve (AUC), using a Quadratic Discriminant Analysis classifier for both the CG and the PZ. Experiments on a data set of 22 subjects showed that applying feature selection resulted in a better accuracy than using the whole set of textural feature. The resulting AUC under the receiver operating characteristic (ROC) curve were 0.86 and 0.73 for CG cancer and PZ cancer, respectively. Hambrock et al. [12] presented a CAD system to help radiologists in differentiating malignant lesions from benign ones in both the TZ and the PZ. Two linear discriminant analysis classifiers, one for the PZ and the other for the TZ, were used to estimate malignancy likelihood using ADC maps and DCE-based features extracted from regions of interest. The experimental results on a data set of 34 patients showed that the use of their CAD system raises the accuracy of the diagnosis for less-experienced radiologists in terms of AUC from 0.81 to 0.91, which is equal to the accuracy for experienced radiologists. Litjens et al. [13] proposed a multiparametric CAD system for prostate cancer diagnosis from DW-MRI, T2-weighted MRI, DCE-MRI, and proton density-weighted MRI. The diagnosis is performed in two steps: first, initial candidate regions are detected. Then, those regions are classified to generate cancer likelihood maps. For classification, the random forest classifier was used and an AUC of 0.91 was achieved. Kwak et al. [14] used DW-MRI at a high b-value with T2-weighted MRI in their proposed CAD system. They utilized a textural feature selection approach of three-stages to obtain the features with the best discriminative capabilities. The resulting AUC was 0.89. Peng et al. [15] evaluated the correlation between a number of features extracted from multiparametric MRI and the aggressiveness of the cancer. Their experiments demonstrated a correlation between ADC values and Gleason score. This correlation was confirmed in a recent study [16].

There are two main limitations of the developed CAD systems for prostate cancer diagnosis from DW-MRI. First, most of these CAD systems only use images acquired at a certain b-value. These b-values are not consistent and differ from one system to another. Therefore, there is no agreement on which b-value will provide the best diagnosis. Second, most investigators just use imaging markers and do not integrate them with the current clinical biomarkers, which may affect the final accuracy of the diagnosis.

Thus, a need continues to exist in the art for CAD systems that improve the diagnosis capability of prostate cancer.

SUMMARY OF THE INVENTION

In an embodiment of the invention, a method for diagnosing prostate cancer is presented. The method includes obtaining magnetic resonance imaging prostate data at a plurality of b-values, processing the magnetic resonance imaging prostate data through a plurality of autoencoders to create a plurality of imaging output probability data. Each of the plurality of autoencoders processes the magnetic resonance imaging prostate data associated with only one of the plurality of b-values. The method further includes organizing the plurality of imaging output probability data into an input vector—a one-dimensional list of the imaging output probability data—and processing the input vector through an autoencoder to generate a diagnosis of prostate cancer.

In another embodiment of the invention, the previously mentioned method for diagnosing prostate cancer is modified so that the input vector also includes biological output probability data. The biological output probability data is created by a method that includes obtaining biological data from a biological value test and processing the biological data through a data classifier.

In another embodiment of the invention, a system for diagnosing prostate cancer is presented. The system includes one or more processors and memory containing program code. The program code is configured so that when it is executed by at least one of the one or more processors, it causes the system to process magnetic resonance imaging prostate data through a plurality of autoencoders to create a plurality of imaging output probability data. Each of the plurality of autoencoders processes the magnetic resonance imaging prostate data associated with only one of a plurality of b-values. The system is further configured to organize the plurality of imaging output probability data into an input vector—a one-dimensional list of the imaging output probability data—and process the input vector through an autoencoder to generate a diagnosis of prostate cancer.

In another embodiment of the invention, the previously mentioned system for diagnosing prostate cancer is modified so that the input vector also includes biological output probability data. The biological output probability data is created by further causing the system to process biological data through a data classifier.

The above summary may present a simplified overview of some embodiments of the invention in order to provide a basic understanding of certain aspects of the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

FIG. 2A is a schematic view of an exemplary feature extraction process for imaging-based features FIG. 2B is a schematic view of an exemplary feature extraction process for biological value-based features

DETAILED DESCRIPTION OF THE INVENTION

Embodiments of the invention comprise methods, systems, and computer program products for analyzing medical images (e.g., prostate image scans) of a medical imaging scan and analyzing biological values (e.g., prostate specific antigen levels) of a clinical biological test. The limitations of existing diagnostic methods are addressed by integrating imaging markers with clinical biomarkers to provide an accurate and robust system for early diagnosis of prostate cancer. DW-MRI data collected at multiple b-values may be used to reduce sensitivity to the selection of a b-value. A deep learning technique may be used to fuse images acquired at multiple b-values with clinical biomarkers to provide a diagnosis of prostate cancer.

In some embodiments of the invention, medical images for a magnetic resonance image (MRI) scan of a prostate may be analyzed, and a probable diagnosis of cancer may be specified. In other embodiments, the probable diagnosis of cancer based on the MRI scan may be combined with a probable diagnosis of cancer based on a clinical biological test, resulting in a final probable diagnosis of cancer. Embodiments of the invention may analyze a prostate based on a series of classification stages to determine the probability cancer in the prostate. Some additional details regarding some of the techniques described herein are provided in I. Reda, A. Khalil, M. Elmogy, A. Abou El-Fetouh, A. Shalaby, M. Abou El-Ghar, A. Elmaghraby, M. Ghazal, and A. El-Baz, "Deep Learning Role in Early Diagnosis of Prostate Cancer," which is incorporated by reference in its entirety. An additional related disclosure may be found in I. Reda, A. Shalaby, M. Elmogy, A. Aboulfotouh, F. Khalifa, M. Abou El-Ghar, G. Gimelfarb, and A. El-Baz, "Image-Based Computer-Aided Diagnostic System for Early Diagnosis of Prostate Cancer," which is also incorporated herein by reference.

Figure 1:
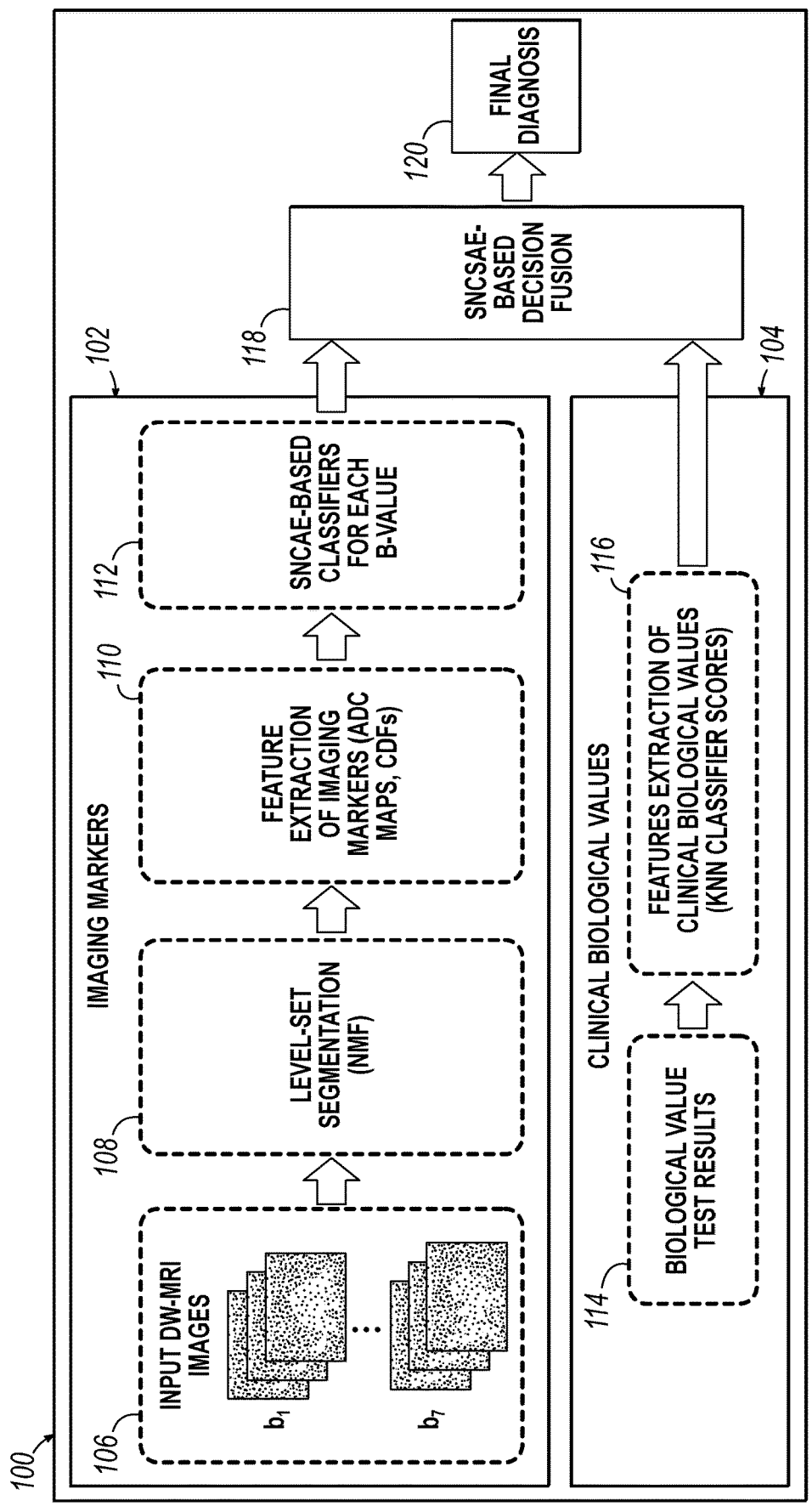
FIG. 1 is a schematic view of a computer aided diagnostic (CAD) process including an image processing component, a biological value processing component, a fusion encoder, and a final diagnosis component.

FIG. 1 depicts a computer aided diagnostic (CAD) process 100 in accordance with an embodiment of the invention. Process 100 includes both image processing 102 and biological processing 104. Image processing 102 begins with delineating the prostate region acquired from the prostate scan images 106 using a level-set segmentation model 108. In an exemplary embodiment of this model, the evolution of the level-set may be guided by a non-deterministic speed function that employs non-negative matrix factorization (NMF). The NMF may fuse DW-MRI intensity information, probabilistic shape prior, and spatial voxels interactions. The resulting segmentation accuracy of the developed segmentation model in terms of Dice similarity coefficient and average Hausdorff distance is about 86.89% and 5.72 mm, respectively. More information about the NMF-employed segmentation model and comparisons with other segmentation models can be found in previous work [17].

In accordance with aspects of the invention the imaging feature extractor 110 extracts, normalizes, and smooths DW-MRI intensity-based features, such as apparent diffusion coefficients (ADCs), using a generalized Gaussian Markov random field (GGMRF) model. Then, the ADCs are globally described using a cumulative distribution function (CDF) of size 100. The DW-MRI intensity-based features are then classified by level-set classifier 112. In accordance with another aspect of the invention, in conjunction with image processing 102, biological processing 104 is also executed. Biological results 114 are acquired and extracted by a biological feature extractor 116. The classified DW-MRI intensity-based features may then be integrated with the biological features for better accuracy of diagnosis as compared to systems lacking this feature. Finally, both the DW-MRI intensity-based features and the biological features are then fed into a stacked non-negatively constrained sparse autoencoder (SNCSAE), fusion encoder 118, to predict the diagnosis of the input prostate volume as either benign or malignant through a two-stage classification and diagnosis 120.

Imaging Features and Clinical Biomarkers

Referring now to FIGS. 2A and 2B, discriminating features may be estimated from the delineated prostate region to differentiate between cancerous and benign prostates, as shown in the embodiment captured by imaging feature extraction 210 and biological feature extraction 220. Prostate image case 212 may be segmented by non-negative matrix factorization (NMF) segmentation 214. Subsequently, a DW-MRI intensity-based feature, such as an apparent diffusion coefficient (ADC), may be realized during calculation and smoothing 216 by measuring the difference between two DW-MRI data images. For example, one of the data images is used as the baseline ($b_0$) and the other image is acquired at a higher b-value. The ADC map is the set of ADC values at every voxel, and may be calculated using the following equation:

$$ADC(x, y, z) = \frac{\ln \frac{S_0(x, y, z)}{S_1(x, y, z)}}{b_1 - b_0} \qquad \text{Eq. (1)}$$

where $S_0$ and $S_1$ are the intensities obtained respectively at the $b_0$ and $b_1$ b-values. It has been demonstrated that the ADC maps are effective in distinguishing between cancerous and benign cases, as benign prostates have a higher average ADC than cancerous ones [18]. The whole ADC maps for all cases at a given b-value are then normalized and refined, during calculation and smoothing 216, using a GGMRF model with a multi-voxel (e.g., 26-voxel) vicinity to eliminate any discrepancy and maintain continuity. Additionally, continuity of the constructed ADC volume may be amplified by using the maximum a posteriori (MAP) estimates. To globally describe the entire ADC volume, cumulative distribution functions (CDFs) of the processed ADC maps for each case may be calculated during cumulative distribution function extraction 218. Like ADC maps, these constructed cumulative distribution functions are able to distinguish between cancerous and benign prostates. Using these constructed CDFs as inputs to the SNCSAE-based classifiers instead of the prostate volumes provides several advantages. For example, these constructed CDFs may have a unified size. Therefore, their use may overcome the challenge related to the variable sizes of different prostate volumes. In addition, due to the small size of these CDFs, they may reduce the time required for training the SNCSAE-based classifiers as well as the time required for classification.

In accordance with another feature of the invention, biological feature extraction 220 is performed in parallel with CDF extraction. That is, biological values are combined with the image processing for greater accuracy. In one embodiment, a PSA marker is used. PSA test results 224 based on prostate cancer test 222 are transformed into a diagnostic probability through a classification step. In one embodiment, the PSA value is classified using K-nearest neighbor (KNN) classifier 226. KNN classifier 226 may be a good choice for low-dimensional data, which is usually the case of the PSA screening results. Other classifiers may be used as well. Subsequently, the initial diagnostic probabilities of several (e.g., seven) different b-values estimated using SNCSAEs that employ ADC-CDFs are then integrated with the PSA-based probabilities to increase the diagnostic accuracy of the prostate cancer diagnosis, resulting in benign score 228 or malignant score 230. While the embodiments described herein may employ a benign/malignant dichotomy for diagnostic scoring for descriptive purposes, alternative embodiments may use other classifiers and provide different diagnostic scoring options. SNCSAE-based Classification In an exemplary embodiment of process 100 of the invention, the classification of prostates into malignant or benign may be obtained by integrating the biological data, such as PSA screening results, with a two-phase structure of a stacked non-negatively constrained sparse autoencoder (SNCSAE). In the first phase, the one or more (e.g., seven) SNCSAE-based classifiers are employed. More specifically, one SNCSAE is deployed for each of the b-values, which may have a range of sizes (e.g., 100 to 700 s/mm$^2$). The individual b-value SNCSAE's are employed to determine an initial classification probability of the prostate case. In the second phase, another SNCSAE is utilized with the results from the first phase. More specifically, the resulting initial classification probabilities of the first phase classifiers, in addition to the PSA-based classification probabilities, are concatenated to form an initial classification probability vector. This vector is then fed into another SNCSAE-based classifier to determine the final classification of the prostate case.

Each SNCSAE compresses the cumulative distribution functions, which may be of size 100, at a certain b-value inputted into it in order to grasp the most noticeable variations. Each SNCSAE is constructed by linking the final hidden layer with a softmax classifier. Each SNCSAE is first pre-trained one layer at a time using greedy unsupervised pre-training [19]. Then, a supervised fine tuning of one or more SNCSAE layers is performed using error backpropagation to minimize the total loss for the given training data. A neural network is then used to learn efficient coding in an unsupervised manner. For example, an autoencoder is one basic unsupervised feature learning algorithm that may be used with embodiments of the invention. Then, non-negatively constrained sparse autoencoders (NCSAE), are used to impose non-negativity and sparsity constraints for learning robust feature representations. In addition, a SNCSAE deep learning network architecture is constructed by layer-wise stacking of multiple NCSAE.

An autoencoder—a type of neural network—is a basic learning component of the SNCSAE used in the invention. An autoencoder includes three layers: the input layer, the hidden layer, and the output layer. Each layer may have a number of nodes, and a node in a given layer may be fully connected to all the nodes in the successive layer. The objective of an autoencoder is to learn a precise compressed representation of input data that can be used at a later stage to reconstruct the input data. In general, an autoencoder has two steps, including encoding and decoding. The encoding layers hierarchically decrease the dimension of their inputs into codes to capture the most essential representations. The decoding layers then try to restore the original input from the codes in the hidden layers.

Figure 3A:
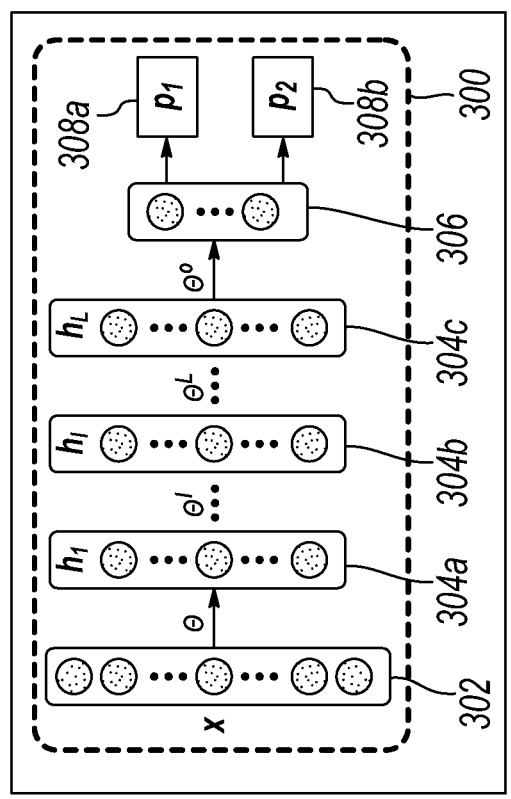
FIG. 3A is a schematic view of a multi-layer stacked non-negatively constrained sparse autoencoder (SNCSAE) classifier.
Figure 3B:
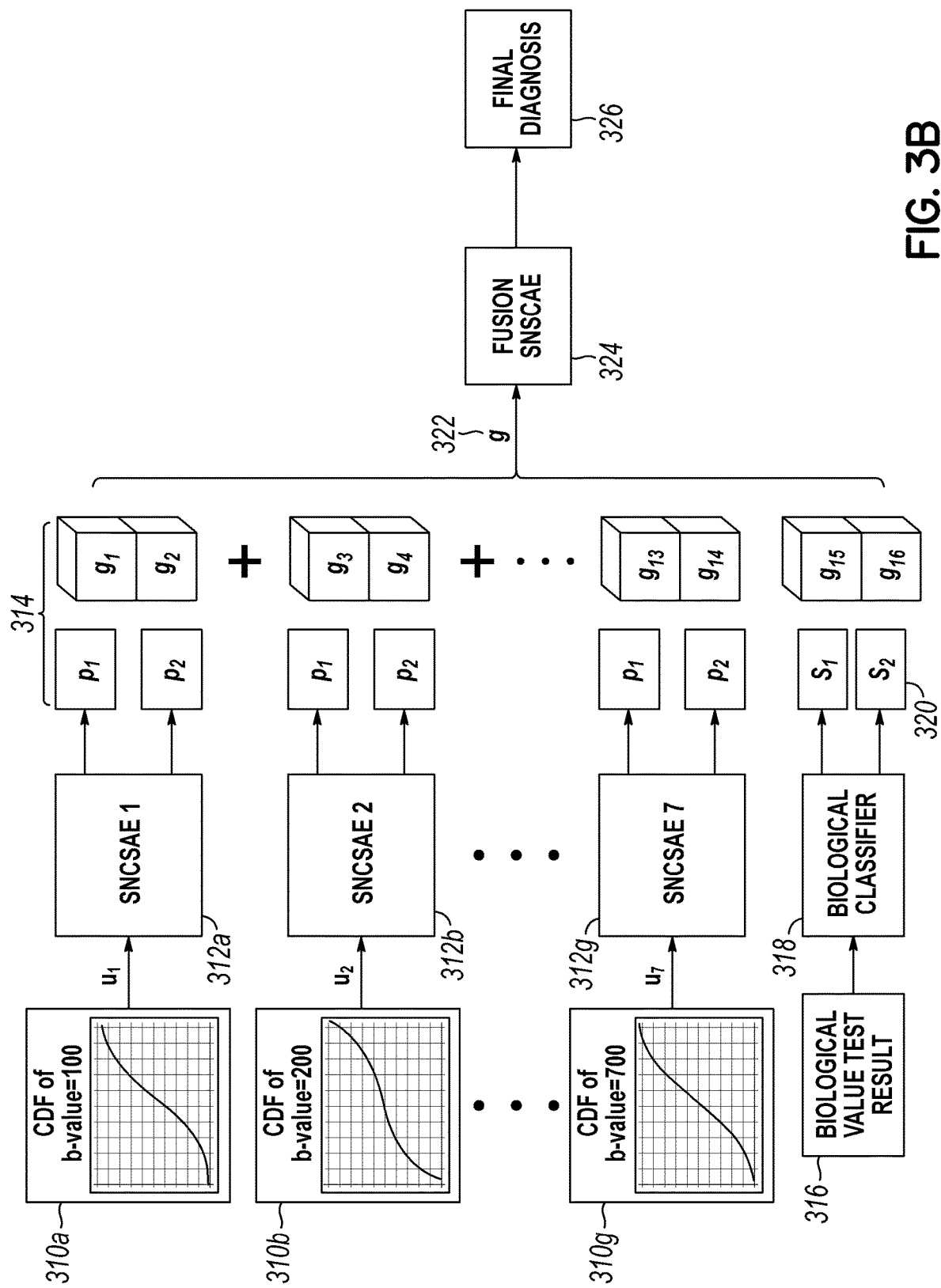
FIG. 3B is a schematic view of a two-phase implementation for providing a diagnosis that uses one or more SNCSAE classifiers.

Referring now to FIGS. 3A and 3B, an autoencoder and the two-stage classification in accordance with the invention are illustrated. FIG. 3A illustrates a general structure for the SNCSAE, as used in stages of the invention. FIG. 3B illustrates the two-stage classification in accordance with the invention. Given an n-dimensional column vector $x=[x_1, \ldots, x_n]^T$ of input data, the autoencoder may first encode the input data into an m-dimensional column vector $h=[h_1, \ldots, h_m]^T$ of hidden feature representations by the nonlinear activation function $\sigma(\ldots)$, which may be defined as:

$$h_j = \sigma((\Theta_j^e)^T X) \equiv \sigma\left(\sum_{i=1}^n \theta_{j:i}^e x_i\right) \quad \text{Eq. (2)}$$

where $\Theta = \{\Theta_j^e, \Theta_j^d: j=1, \ldots, s; i=1, \ldots, n\}$ denotes a set of vectors of trainable coefficients for the layers of encoding (e) and decoding (d) of a given AE, T denotes vector transposition, and $\sigma(\phi)=1/(1+\exp(\phi))$ is a sigmoid function whose outputs are in the interval [0,1].

The autoencoder may reconstruct an approximation of the original input from the hidden feature representation. To learn a compressed representation that can help find out concealed structures of high-dimensional data, and to avoid trivial solution of the minimization of the loss function of Eq. (3), such as identity transformation, it is required that the hidden layer dimension be less than the input dimension, i.e., m<<n. Given a training set of K samples, the autoencoder is trained to find the optimal coefficients of all connections by minimizing the loss function that describes the discrepancy between each input vector $x_k$; $k=1, \ldots, K$, and its reconstruction vector, b (3) $\hat{x}_{\Theta:k}$ over the entire training set.

$$J_{AE}(\Theta) = \frac{1}{2K} \sum_{k=1}^K \|\hat{x}_{\Theta:k} - x_k\|^2 \quad \text{Eq. (3)}$$

Here, the average sum of squares-of-differences may represent the reconstruction error. The minimization of that reconstruction error indicates that the learned features preserve a significant amount of information about the input which can be a required criterion of precise representation of the original input [20].

NCSAE may impose additional constraints on the basic autoencoder, such as, non-negativity and sparsity constraints [20]. The non-negativity constraint causes the autoencoder to learn additive part-based representation of its input data, while the sparsity constraint may cause the average activation of each hidden unit over the entire training data set to be infinitesimal to improve the probability of linear separability [21]. Imposing the non-negativity constraint on the autoencoder may result in more precise data codes during the greedy layer-wise unsupervised training and improved accuracy after the supervised fine-tuning [22]. Mathematically, the loss function of Eq. (3) may be extended by the addition of one or more penalty terms in an attempt to lower the number of negative coefficients and compel sparsity of the NCSAE. Some exemplary terms that may be imposed are a quadratic negative coefficient penalty, $f(\theta_j)=(\min\{0, \theta_{ij}\})^2$; $i=1, \ldots, n$, and Kullback-Leibler (KL) divergence, $J_{KL}(h_{\Theta^e};\rho)$, between the hidden codes, $h_{\Theta^e}$, achieved using the encoding coefficients $\Theta^e$ of the training data set, and a small positive constant value, $\rho$, close to 0 representing the target average activation. The value of $\rho$ may be chosen to be small as a small $\rho$ can lead to complete and non-redundant features be learned, as shown by [23]:

$$J_{NCSAE}(\Theta) = J_{AE}(\Theta) + \alpha \sum_{j=1}^s \sum_{i=1}^n f(\theta_{j:1}) + \beta J_{KL}(h_{\Theta^e}; \rho) \quad \text{Eq. (4)}$$

The parameters $\alpha \geq 0$ and $\beta \geq 0$ may control the amount of contributions of the non-negativity and the sparsity terms to the total loss function, $J_{NCSAE}(\Theta)$, and $$J_{KL}(h_{\Theta^e}, \rho) = \sum_{j=1}^{s} h_{\Theta^e;j} \log\left(\frac{h_{\Theta^e;j}}{\rho}\right) + (1 - h_{\Theta^e;j})\log\left(\frac{1 - h_{\Theta^e;j}}{1 - \rho}\right) \quad \text{Eq. (5)}$$

It has been determined that a deep learning architecture may have the capability of learning complex and highly non-linear features from data [23,24]. In order to attempt to learn high-level features from data, namely input vector 302, NCSAE is used as a building block to construct a multi-layer architecture of NCSAEs, multi-layer SNCSAE 300. In this architecture, the output vector from a low-level NCSAE (e.g., NCSAE layer 304a) may be used as input to a high-level NCSAE (e.g., NCSAE layer 304b). In addition, the output of the final NCSAE (e.g., NCSAE layer 304c) may be inputted to a softmax regression classifier such as softmax classifier 306. A good technique to train such deep learning architectures, which may avoid certain limitations associated with full supervised training, can be to first pre-train the network one layer at a time using the unsupervised greedy algorithm.

In a particular embodiment, the first and second NCSAEs, which may be the first and second layers of SNCSAE, can be pre-trained separately to minimize the total loss function of Eq. (4). This may result not only in decreasing the reconstruction error, but also in increasing the number of non-negative coefficients and the sparsity of the hidden representations. The outputs of the second NCSAE, $h^{[2]} = \sigma(\Theta_{[2]}^{e^T} h^{[1]})$, may be inputted to the softmax classifier, as best shown in FIG. 3A, in order to estimate the classification of the prostate case at a certain b-value as a probability, a benign probability 308a, and/or a malignant probability 308b, of each output class, c=1,2 using:

$$p(c; \Theta_{o:c}) = \frac{\exp(\Theta_{o:c}^T h^{[2]})}{\exp(\Theta_{o:1}^T h^{[2]}) + \exp(\Theta_{o:2}^T h^{[2]})}; \quad \text{Eq. (6)}$$

$$c = 1, 2; \sum_{c=1}^{2} p(c; \Theta_{o:c}; h^{[2]}) = 1.$$

This unsupervised layer-wise training aims to minimize the negative log-likelihood $J_o(\Theta_o)$ of the training classes, appended with the penalization of negative coefficients:

$$J_o(\Theta^o) = -\frac{1}{K}\sum_{k=1}^{K} \log p(c_k; \Theta_{o:c}) + \nu \sum_{c=1}^{2}\sum_{j=1}^{s_2} \theta_{o:c;j}^{-} \quad \text{Eq. (7)}$$

A supervised fine-tuning of all SNCSAE layers may follow the unsupervised pre-training to ensure that the learned representations can be discriminative [25]. This supervised fine-tuning may be performed on the training data using error backpropagation through the layers and with the penalization of the negative coefficients of the softmax classifier only. In an exemplary embodiment of the invention, the parameters $\alpha=0.003$, $\beta=5$, and $\rho=0.5$ were selected empirically based on comparative experiments. However, other values for these parameters may be utilized in alternative embodiments of the invention.

In accordance with one feature of the invention, FIG. 3B refers to a two-phase structure that implements one or more stacked non-negatively constrained sparse autoencoders (SNCSAE) in each phase. In one embodiment of the first phase, the image input data 310a-g to each of the SNCSAEs is a cumulative distribution function (CDF) at a certain b-value (e.g., 100 to 700 s/mm² in increments of 100). That is, there exists an SNCSAE and a CDF for each b-value. Additionally, each CDF is of a certain size (e.g., 100), and the size is uniform amongst all CDFs. As each image input data 310 is processed by its respective stacked non-negatively constrained sparse autoencoder, SNCSAE 312a-g, the size of the input vector is decreased. For example, the first layer of a SNCSAE 312 may decrease to $s_1=50$, which may subsequently decrease by the following layer to $s_2=5$, and may be further reduced by the final softmax classifier in SNCSAE stack 312 to $s^*=2$ probabilities.

In accordance with another feature of the invention, biological data is combined with image data and then subjected to the second phase of autoencoding. In one embodiment, only image data is used for the multi-phase use of the stacked non-negatively constrained sparse autoencoder (SNCSAE). In another embodiment, biological data is combined with image data. In the second phase of the classification under the current embodiment shown in FIG. 3B, biological results 316 may be processed by low-dimensional data classifier 318 to yield biological-based probabilities 320. That is, the biological results are converted into a form than can be incorporated into a probability input vector. Both biological-based probabilities 320 and the output probabilities of each of the SNCSAEs, SNCSAE-based probabilities 314, of the first stage may be concatenated to form an initial probability vector $g=[g_1, \ldots, g_{16}]$ 322. This probability vector (g) may be used as an input to a new stacked non-negatively constrained sparse autoencoder (SNCSAE), referred to herein as fusion SNCSAE 324, to determine the ultimate classification or final diagnosis 326 of the prostate case as a probability for each output class, c, using the following formula:

$$p_t(c; \Theta_{o:c}^t) = \frac{\exp((\Theta_{o:c}^t)^T g_t)}{\sum_{c=1}^{C} \exp((\Theta_{o:c}^t)^T g_t)}; \quad \text{Eq. (8)}$$

$$c = 1, 2$$

Experimental Results

Figure 4:
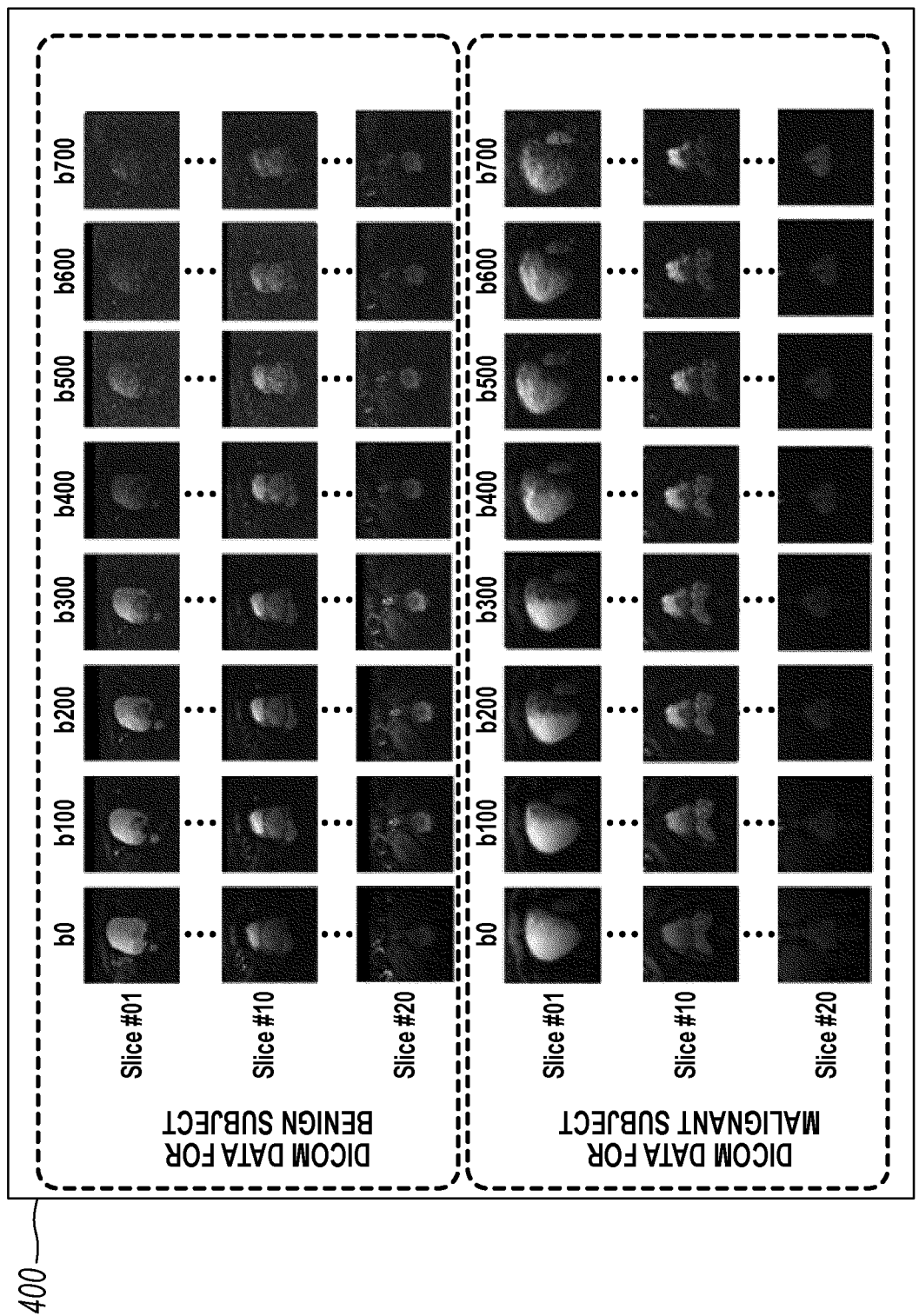
FIG. 4 is a graphical view of DW-MRI images from two subjects at different b-values.

Analysis was conducted on DW-MRI data sets acquired from 18 patients (nine benign and nine malignant). Each patient was diagnosed using a biopsy. Biopsies were carried out using a systematic approach with 11 cores taken from the whole prostate. PSA blood samples were used as the clinical biological value, the samples being extracted from all 18 patients one week before the subjects were scanned by a DW-MRI scanner. A conventional venous blood draw procedure was used to obtain 3 mL from each patient. FIG. 4 shows DW-MRI images 400 from two subjects at different b-values.

To highlight the benefit of combining clinical biological values with DW-MRI features, several experiments that used clinical biological values only, DW-MRI features only, or a combination of both clinical biological values and DW-MRI features, were conducted. For the DW-MRI experiment, the discriminating characteristics of benign and cancerous cases are captured from the DW-MRI data sets by training 7 different SNCSAEs, one SNCSAE for each of the 7 different b-values (100, 200, . . . , 700 s/mm$^2$). The features adopted for the diagnosis are the cumulative distribution functions of the processed apparent diffusion coefficient volumes, of the delineated prostates. These are estimated at 7 different b-values in accordance with the above description. A combination of lower b-values and higher b-values was utilized because lower b-values may show perfusion while higher b-values may show diffusion. It is believed that both perfusion and diffusion can be used to discriminate malignant tumors from benign ones. Results are mixed with the middle-ranged b-values (i.e., they do not represent clear perfusion nor clear diffusion). In accordance with one feature of the invention, it is desirable to have a combination of lower and higher b-values to show good results for early diagnosis of prostate cancer. Hence, data is acquired at multiple b-values to capture both perfusion and diffusion—leading to more accurate results.

Figure 5:
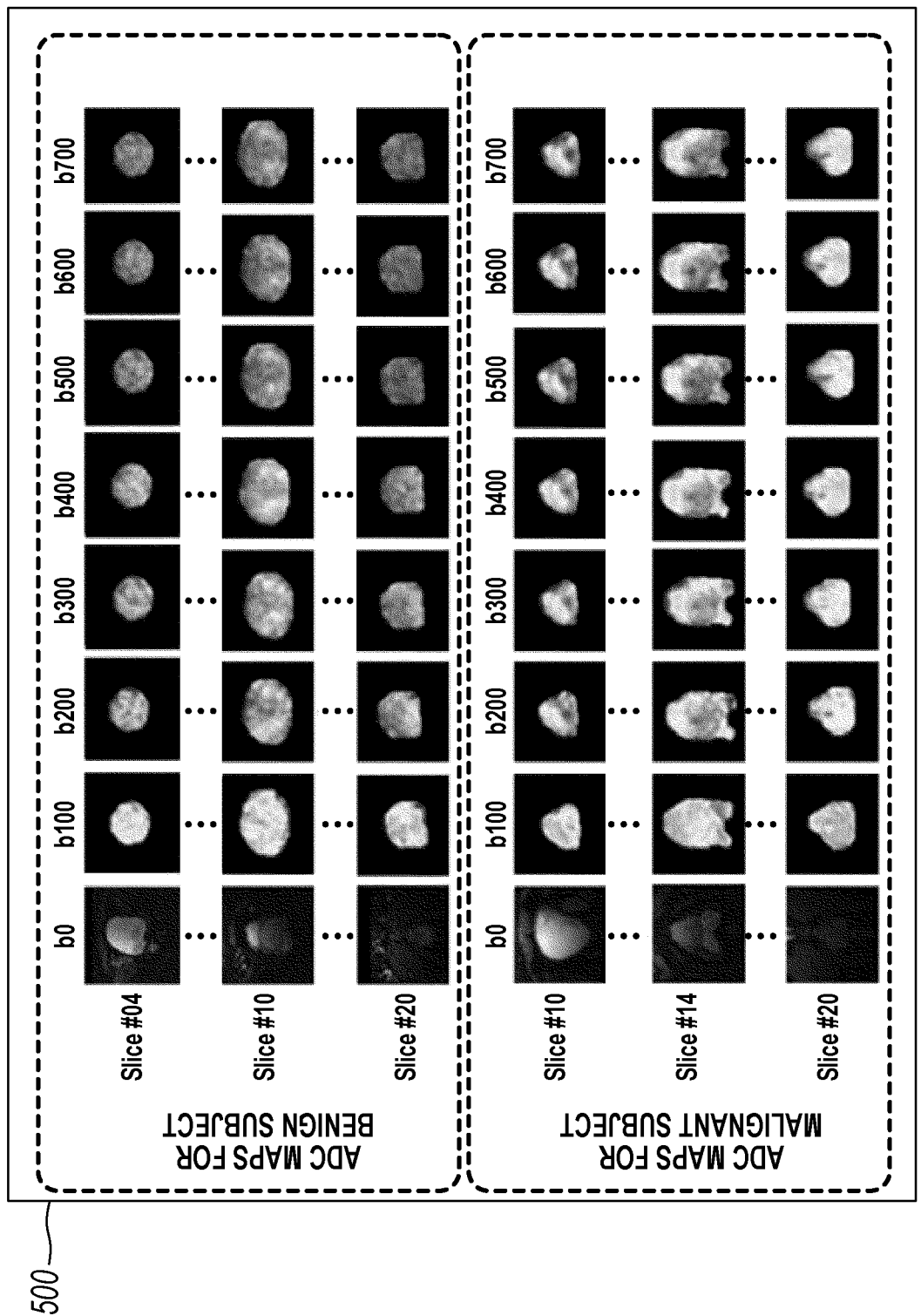
FIG. 5 is a graphical view of ADC images from two subjects at different b-values.

FIG. 5 illustrates ADC color maps 500 of two subjects at different b-values. In order to test the effect of each feature (e.g., CDFs of each b-value), each SNCSAE of the first-stage of the classification, corresponding to a specific b-value, was first individually trained and tested for each feature. To evaluate the accuracy of this experiment, a leave-one-subject-out (LOSO) cross validation was performed for each SNCSAE with all 18 DW-MRI data sets. The diagnostic accuracy for each SNCSAE using the LOSO cross validation is reported in Table 1.

In order to make a global classification decision based only on DW-MRI, in accordance with one embodiment of the invention all diffusion-based probabilities from the 7 SNCSAEs were concatenated to form an input vector. That image data-only input vector was then fed into a new SNCSAE at the next stage. The resulting accuracy after this fusion was 88.89% (sensitivity=88.89% and specificity=88.89%). Moreover, a three-fold cross validation was performed using the DW-MRI data sets at each b-value. The diagnostic accuracy at each b-value using three-fold cross validation at 7 b-values is reported in Table 2.

TABLE 1

| SNCSAE | Accuracy | Sensitivity | Specificity |
|---|---|---|---|
| SNCSAE 1 (b-value = 100) | 77.8% | 77.8% | 77.8% |
| SNCSAE 2 (b-value = 200) | 66.6% | 77.8% | 55.6% |
| SNCSAE 3 (b-value = 300) | 72.2% | 77.8% | 66.7% |
| SNCSAE 4 (b-value = 400) | 72.2% | 77.8% | 66.7% |
| SNCSAE 5 (b-value = 500) | 72.2% | 77.8% | 66.7% |
| SNCSAE 6 (b-value = 600) | 83.3% | 88.9% | 77.8% |
| SNCSAE 7 (b-value = 700) | 83.3% | 88.9% | 77.8% |

TABLE 2

| SNCSAE | 1$^{st}$ fold | 2$^{nd}$ fold | 3$^{rd}$ fold | Average |
|---|---|---|---|---|
| SNCSAE 1 | 66.7% | 83.3% | 66.7% | 72.2% |
| SNCSAE 2 | 66.7% | 83.3% | 50% | 66.7% |
| SNCSAE 3 | 66.7% | 50% | 83.3% | 66.7% |
| SNCSAE 4 | 66.7% | 50% | 83.3% | 66.7% |
| SNCSAE 5 | 83.3% | 50% | 66.7% | 66.7% |
| SNCSAE 6 | 66.7% | 50% | 100% | 72.2% |
| SNCSAE 7 | 66.7% | 100% | 66.7% | 77.8% |

In accordance with another embodiment of the invention, biological data is used with the image data in the next stage of SNCSAE. For the clinical biological value experiment, PSA screening served as the test. Other biological values and/or tests might also be incorporated in accordance with the invention. Such biological data is further processed, such as using classification processing. Such classification transforms PSA data into a form usable with the image data for forming the vector for use in the next SNCSAE stage. For the PSA values, a K-nearest neighbor (KNN) based classifier might be used, for example. The PSA screening result of each case was transformed into a diagnostic probability using the KNN-based classifier. To apply a KNN-based classifier that identified the prostate status, a LOSO cross validation is used for each subject. The resulting accuracy is shown in Table 3 and illustrates the need to combine other features with the PSA screening results to improve the system accuracy.

TABLE 3

| Classifier | Accuracy | Sensitivity | Specificity |
|---|---|---|---|
| KNN | 77.78% | 55.56% | 100% |

The results from both the image processing and biological value processing were fed into the next stage, or fusion SNCSAE, to determine the final diagnosis of the input prostate as benign or malignant through the inventive two-stage classification process. The overall classification accuracy, sensitivity, and specificity were 94.4%, 88.9%, and 100%, respectively for the LOSO cross validation. The overall classification accuracy, sensitivity, and specificity were 88.9%, 77.8%, and 100%, respectively for the three-fold cross validation. These results emphasize the advantage provided by the invention of integrating imaging (e.g., DW-MRI) and clinical biological (e.g., PSA) results for prostate cancer diagnosis.

In an alternative embodiment of the invention, an alternative neural network might be utilized in the invention. For example, the imaging markers may be fed into a convolutional neural network (CNN) instead of a SNCSAE.

To demonstrate the advantage of using a SNCSAE-based classifier, a comparison was conducted between the SNCSAE-based classifier and two state-of-the-art classifiers, a random forest (RF) classifier and random tree (RT) classifier [31]. Table 4 shows the resulting accuracy, sensitivity, specificity, and AUC of these three classifiers. As is shown in Table 4, the performance of the SNCSAE-based classifier is better than the performance of both the RF and the RT classifiers. This is indicative of the improved diagnostic capabilities of embodiments of the invention using an autoencoder, such as a stacked non-negatively constrained sparse autoencoder (SNCSAE).

Figure 6:
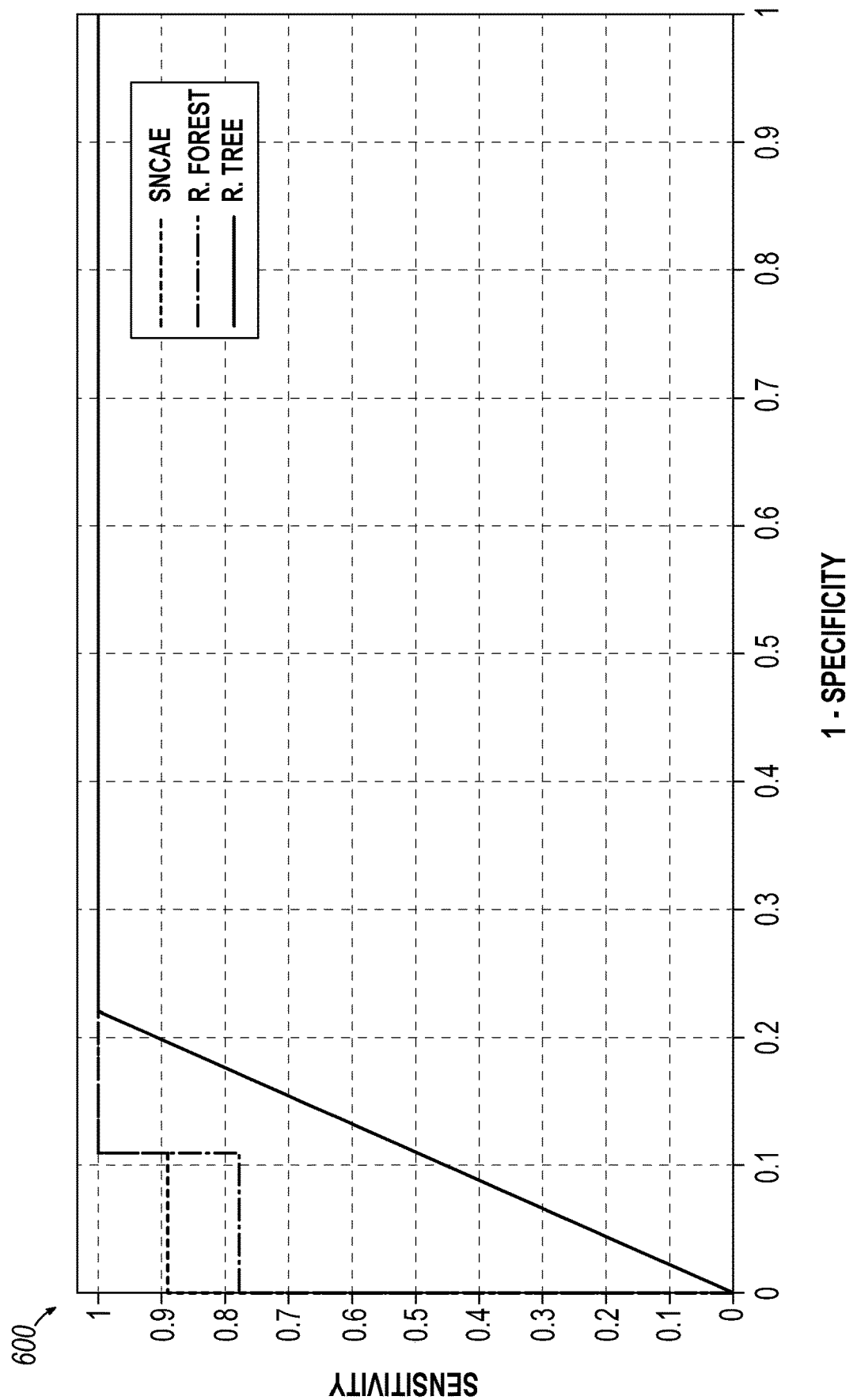
FIG. 6 is a graphical view of an exemplary image that illustrates the receiver operating characteristic (ROC) curve for multiple classifiers.

FIG. 6 depicts an exemplary graph 600 that illustrates the corresponding ROC curve for the SNCSAE-based, RF, and RT classifiers. The 95% confidence interval (CI) was computed using a bootstrapping technique [32]. A random sample of 18 subjects was selected and replacement and the corresponding area under the curve (AUC) computed. The operation was repeated 100 times. The effect of the replacement aspect on the results is that if the misclassified subjects are selected more than one time, then the resulting performance in terms of the AUC is reduced. The resulting 95% CI ranges from 0.79 to 1. In our case, the number of the used subjects is limited. However, the upper bound of 95% CI equals one, which indicates that the accuracy of the presented method, in terms of sensitivity and specificity, can reach 100%, in case of increasing the number of subjects.

Figure 7:
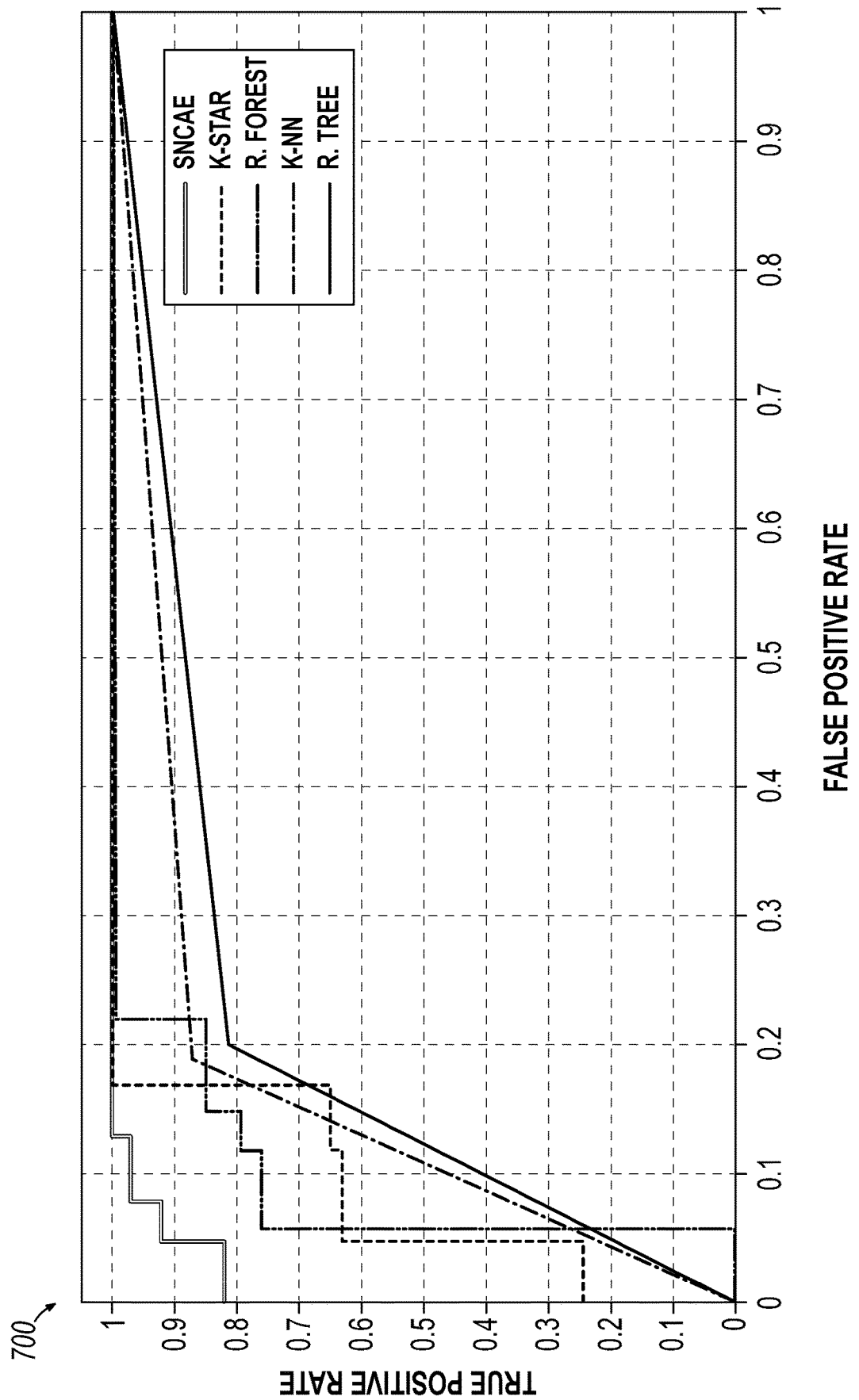
FIG. 7 is a graphical view of an exemplary image that illustrates an advantage of using a SNCSAE classifier in comparison with other classifiers.

FIG. 7 depicts an exemplary graph 700 that highlights the advantage of using a SNCSAE-based classifier in accordance with the invention. In addition to RF and RT classifiers, an advantage can be seen against other ready to use classifiers such as k-star (K*) and K-nearest neighbor (KNN).

Figure 8:
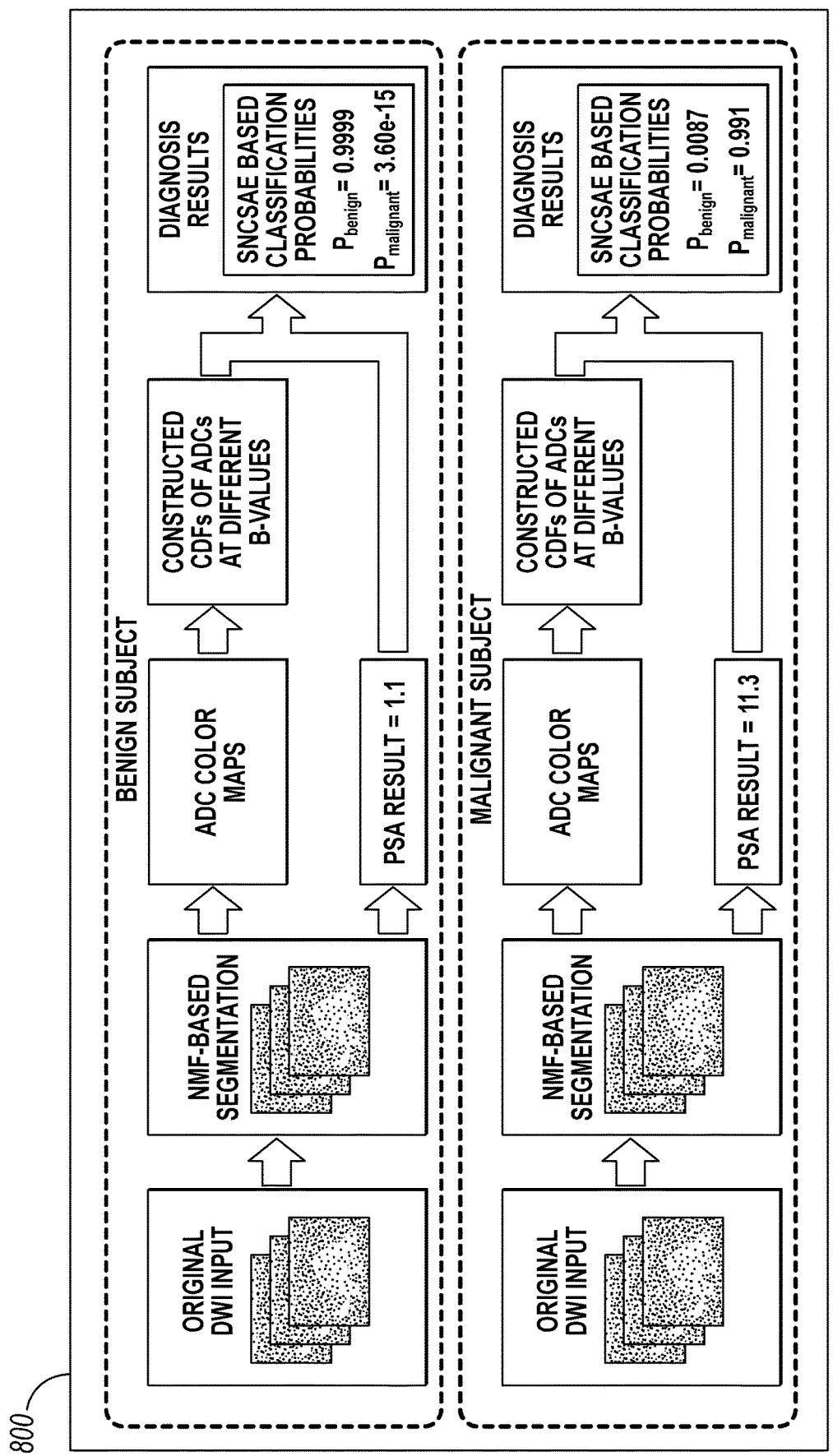
FIG. 8 is a schematic view of an two exemplary applications of the CAD process of FIG. 1

FIG. 8 depicts a process in accordance with an exemplary embodiment of the invention for diagnosing benign and/or malignant prostate cases.

TABLE 4

| Classifier | Accuracy | Sensitivity | Specificity | AUC |
|---|---|---|---|---|
| SNCSAE | 94.4% | 88.9% | 100% | 0.98 |
| RF | 88.9% | 88.9% | 88.9% | 0.97 |
| RT | 88.9% | 100% | 77.8% | 0.88 |

Figure 9A:
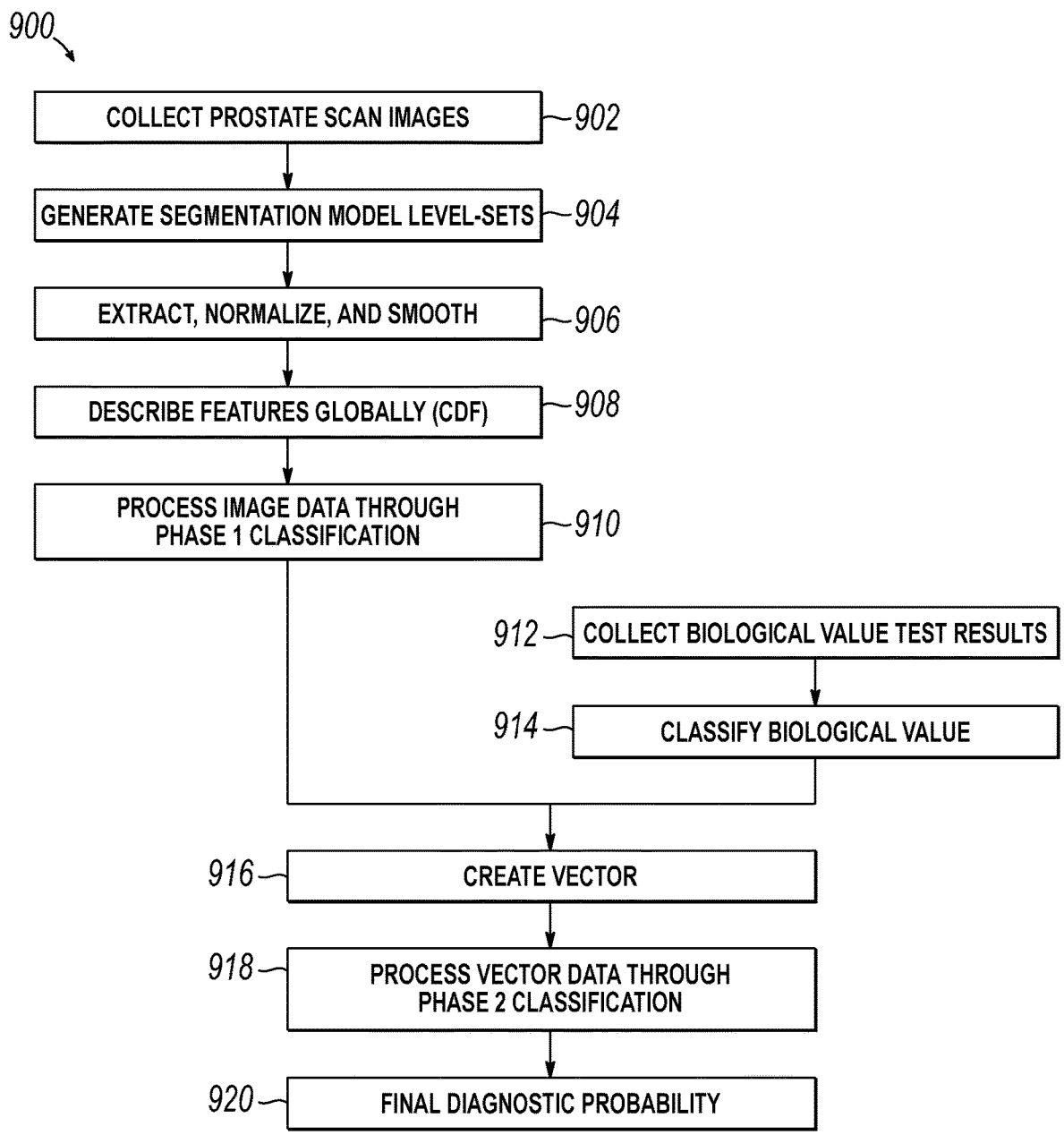
FIG. 9A is a flowchart illustrating a CAD process for analyzing images and biological values that may be executed by the computing system of FIG. 10.

FIG. 9A depicts a flow chart illustrating an exemplary automated CAD process 900 for determining a final diagnostic probability 920 based on prostate scan images 902, biological value test results 912, and analysis thereof, according to an embodiment of the invention. Consistent with embodiments of the invention, both the imaging steps and biological value steps may be performed in parallel.

In block 902, prostate scan images 902 may be collected using DW-MRI technology. The prostate scan images 902 may be collected in sets using different b-values, e.g., seven different b-values. Advantageously, this may improve diagnostic results in cases where no single b-value stands out to provide a better diagnosis of prostate cancer.

In block 904, the process 900 may generate segmentation module level sets for each set of images 902. A non-deterministic speed function, such as one that employs non-negative matrix factorization (NMF), may be combined with a geometric deformable model (i.e., level-sets) to guide the segmentation. This hybrid approach may allow for the fusion of various data from the images received in block 902 (e.g., intensity information, probabilistic shape prior, spatial voxels interactions). In block 906, the process 900 may extract, normalize, and smooth the intensity-based features (i.e., ADC) of the segmented image sets. For example, a generalized Gaussian Markov random field model (GGMRF) with a 26-voxel vicinity might be used for smoothing. Such processing of the ADC enables the elimination of any discrepancies and maintains continuity amongst the segmented image sets.

In block 908, the process 900 may globally describe the resulting information for each set using a function such as a cumulative distribution function (CDF) of a fixed size (e.g., size 100). The cumulative distribution function normalizes the segmented image sets so that prostates of different volumes can be described with a unified size. This is critical because a unified size is required for classification and current unification methods sacrifice accuracy (e.g., truncating the image sets of large prostate volumes, padding the image set of small prostate volumes). Additionally, because the CDF may be of a fixed size, less than the size of the segmented image sets, training time for the classifiers and the actual classification time is reduced.

In block 910, the globalized segmented image sets may enter phase 1 classification 910. This classification yields an imaging diagnostic probability for each set of CDF data for the plurality of b-values in accordance with the invention. Phase 1 classification 910 may include the SNCSAE-based classifier described above, or may use other classifiers (e.g., a CNN). The SNCSAE-based classifier may include one or more layers of classification—e.g., two sequential NCSAE classifier layers followed by a softmax layer.

In block 912, the process 900 may obtain or collect the clinical steps, biological value test results 912, which may be results obtained from numerous exams. Biological value tests may encompass any physical indicator based on a patient and may include, but are not limited to, traditional biological markers (e.g., PSA screening), medical exams (e.g., digital rectal exam, histology imaging), or patient feedback (e.g., pain assessment chart, patient questionnaire).

In block 914, the process classifies the biological value 914 using a classifier, such as a low-dimensional classifier to yield a clinical or biological diagnostic probability. An example of a low-dimensional classifier that may be used by the process 900 may include a K-nearest neighbor (KNN) classifier as described.

In block 916, the process 900 may create a vector where both the imaging diagnostic probabilities, one for each set, and the clinical or biological diagnostic probabilities are concatenated to form an initial classification probability vector. In block 918, the process 900 may run the vector through phase 2 classification. Such as another stage of the autoencoder (SNCSAE) as disclosed. A final diagnostic probability results from the second autoencoder stage as noted in block 920. Phase 2 classification may include the SNCSAE-based classifier described above, or may use other classifiers (e.g., a CNN). With respect to the SNCSAE-based classifier, it may include one or more (e.g., three layers) of classification—two sequential NCSAE classifier layers followed by a softmax layer as disclosed.

Figure 9B:
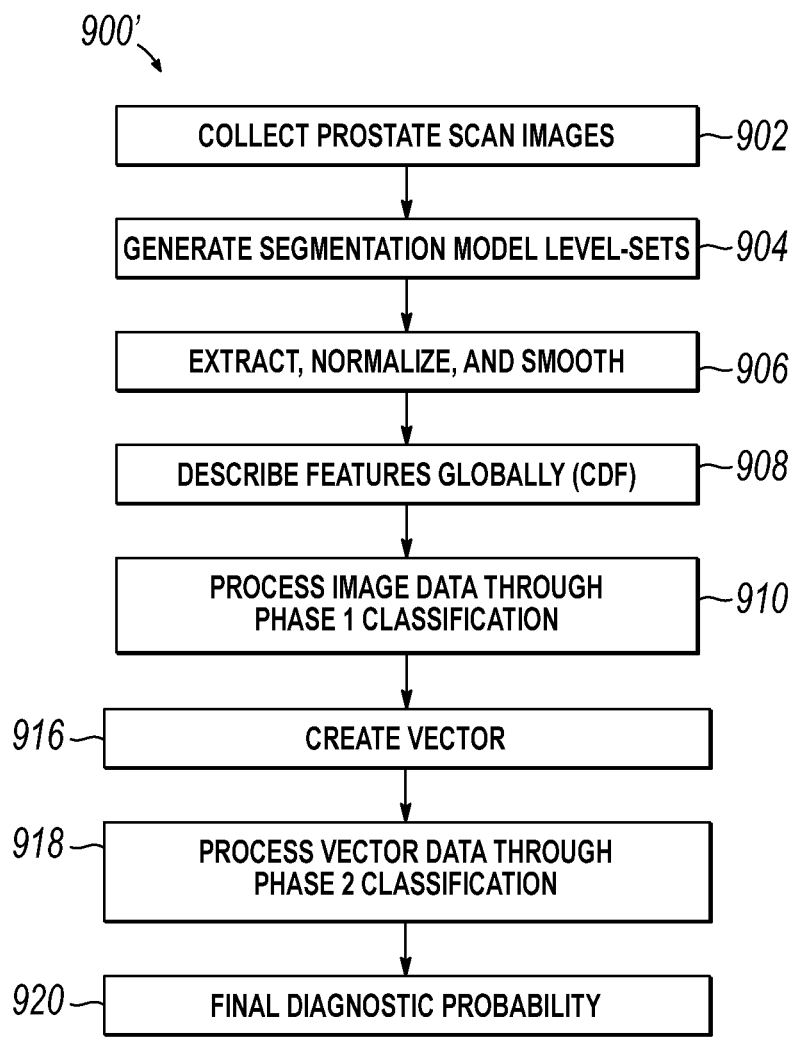
FIG. 9B is a flowchart illustrating a CAD process for analyzing images that may be executed by the computing system of FIG. 10.

FIG. 9B depicts a flow chart of a process 900' for an alternative embodiment of the invention in which the final diagnostic probability is derived from the imaging values while excluding the biological values.

Figure 10:
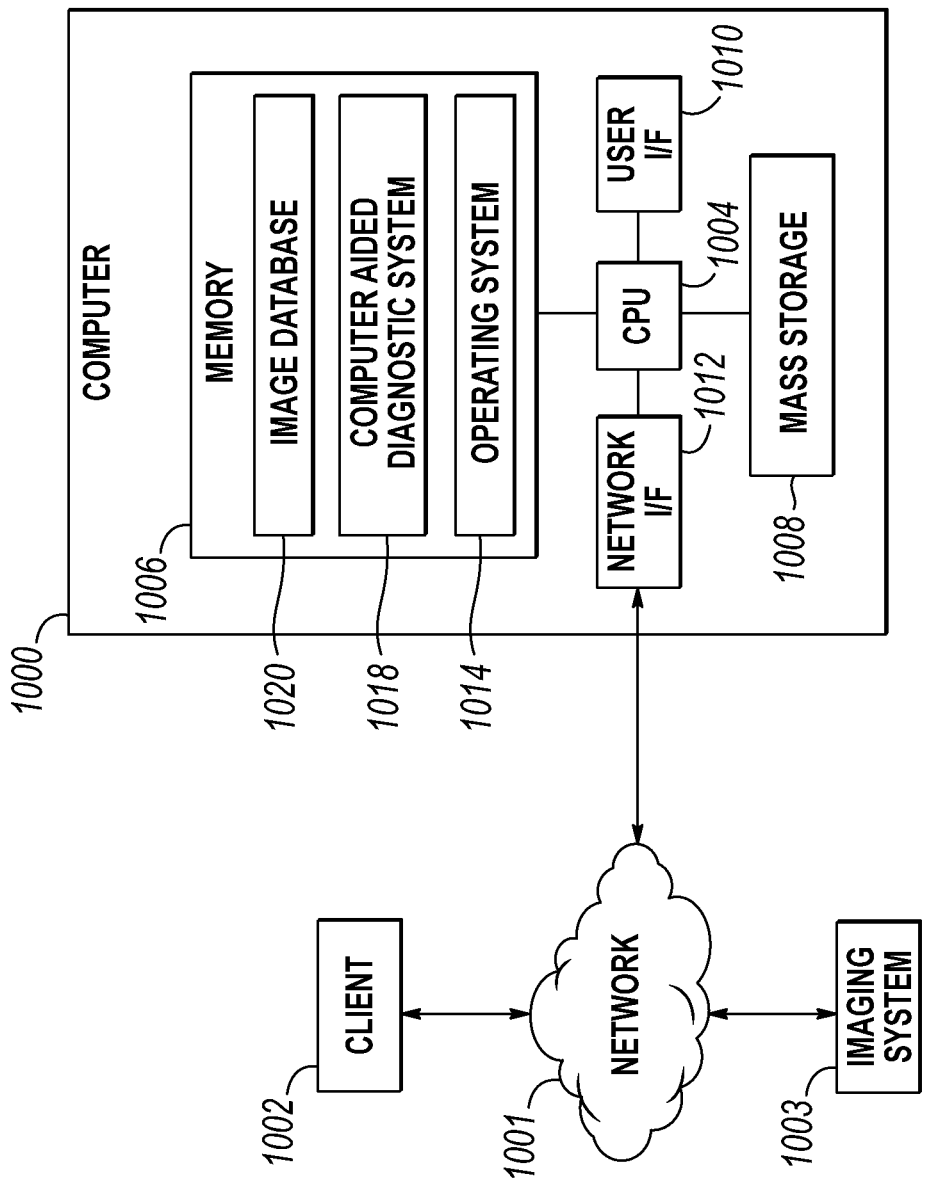
FIG. 10 is a schematic view of an exemplary computing system that may be used to implement various operations associated with embodiments of the invention.

FIG. 10 illustrates an exemplary apparatus 1000 that may be used to implement various operations associated with embodiments of the invention. For example, one or more steps in processes 9A or 9B may be implemented in an automated fashion, utilizing a computer or other electronic device, such as apparatus 1000.

Apparatus 1000 may be implemented as a server or multi-user computer that is coupled via a network 1001 to one or more client computer 1002, as well as an imaging system 1003 (e.g., a DW-MRI scanner). For the purposes of the invention, each computer 1000, 1002 may represent practically any type of computer, computer system or other programmable electronic device. Moreover, each computer 1000, 1002 may be implemented using one or more networked computers (e.g., in a cluster or other distributed computing system). In the alternative, computer 1000 may be implemented within a single computer or other programmable electronic device, for example, within a desktop computer, a laptop computer, a handheld computer, a cell phone, a set top box, etc.

Computer 1000 may include a central processing unit 1004 including at least one microprocessor coupled to a memory 1006, which may represent the random access memory (RAM) devices comprising the main storage of computer 1000, as well as any supplemental levels of memory (e.g., cache memories, programmable or flash memories, read-only memories). In addition, memory 1006 may be considered to include memory storage physically located elsewhere in computer 1000 (e.g., any cache memory in a processor in CPU 1004), as well as any storage capacity used as a virtual memory (e.g., as stored on a mass storage device 1008, on another computer coupled to computer 1000).

Computer 1000 may receive a number of inputs and outputs for communicating information externally. For interface with a user or operator, computer 1000 typically includes a user interface 1010 incorporating one or more user input devices (e.g., a keyboard, a mouse, a trackball, a joystick, a touchpad, a touchscreen, and/or a microphone, among others) and a display (e.g., a CRT monitor, an LCD display panel, an LED display panel, an OLED display panel, a projector, and/or a speaker, among others). Otherwise, user input may be received via another computer or terminal.

For additional storage, computer 1000 may also include one or more mass storage devices 1008—e.g., a floppy or other removable disk drive, a hard disk drive, a direct access storage device (DASD), an optical drive (e.g., a CD drive, a DVD drive, etc.), and/or a tape drive—among others. Furthermore, computer 1000 may include an interface 1012 with one or more networks 1001 (e.g., a LAN, a WAN, a wireless network, and/or the Internet, among others) to permit the communication of information with other computers and electronic devices. It should be appreciated that computer 1000 typically includes suitable analog and/or digital interfaces between CPU 1004 and each of components 1006, 1008, 1010, and 1012 as is well known in the art. Other hardware environments are contemplated within the context of the invention.

Computer 1000 operates under the control of an operating system 1014 and executes or otherwise relies upon various computer software applications, components, programs, objects, modules, data structures, etc., as will be described in greater detail below. Moreover, various applications, components, programs, objects, modules, etc. may also execute on one or more processors in another computer coupled to computer 1000 via network 1001, for example, in a distributed or client-server computing environment, whereby the processing required to implement the functions of a computer program may be allocated to multiple computers over a network.

As an example, computer 1000 may include a computer aided diagnostic (CAD) system program 1018 used to implement one or more of the steps described above in connection with processes 9A or 9B. For the purposes of implementing such steps, an image database 1020, storing DW-MRI prostate scan images, may be implemented in computer 1000. It will be appreciated, however, that some steps in processes 9A or 9B may be performed manually and with or without the use of computer 1000.

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause the computer to perform the steps necessary to execute steps or elements embodying the various aspects of the invention.

Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable storage media include but are not limited to physical, tangible storage media such as volatile and non-volatile memory devices, floppy and other removable disks, hard disk drives, magnetic tape, optical disks (e.g., CD-ROMs, DVDs, etc.), among others.

In addition, various program code described herein may be identified based upon the application within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

Reference in this specification to "one embodiment," "an embodiment," an "example embodiment," etc., indicate that the embodiment described may include a particular feature, structure, or characteristic, but not every embodiment may necessarily include the particular feature, structure, or characteristic. Moreover, such phrases are not necessarily referring to the same embodiment. Further, when a particular feature, structure, or characteristic may be described in connection with an embodiment, it may be submitted that it may be within the knowledge of one of ordinary skill in the relevant art to affect such feature, structure, or characteristic in connection with other embodiments whether or not explicitly described.

The previous detailed description refers to the accompanying drawings that illustrate exemplary embodiments. Other embodiments are possible, and modifications can be made to the embodiments within the spirit and scope of this description. Those of ordinary skill in the relevant art with access to the teachings provided herein will recognize additional modifications, applications, and embodiments within the scope thereof and additional fields in which embodiments would be of significant utility. Therefore, the detailed description is not meant to limit the embodiments described above.

REFERENCES

1. Siegel R L, Miller K D and Jemal A. Cancer statistics, 2016. CA Cancer J Clin 2016; 66(1): 7-30.

2. Ferlay J, Shin H R, Bray F et al. GLOBOCAN 2008, Cancer incidence and mortality worldwide: IARC CancerBase No. 10. Lyon, France: International Agency for Research on Cancer 2010; 2.
3. Mistry K and Cable G. Meta-analysis of prostate-specific antigen and digital rectal examination as screening tests for prostate carcinoma. J Am Board Fam Pract 2003; 16(2): 95-101.
4. Dijkstra S, Mulders P and Schalken J. Clinical use of novel urine and blood based prostate cancer biomarkers: a review. Clin Biochem 2014; 47(10-11): 889-896.
5. Davis M, Sofer M, Kim S S et al. The procedure of transrectal ultrasound guided biopsy of the prostate: a survey of patient preparation and biopsy technique. J Urol 2002; 167(2): 566-570.
6. Hricak H, Choyke P L, Eberhardt S C et al. Imaging prostate cancer: a multidisciplinary perspective 1. Radiology 2007; 243(1): 28-53.
7. Applewhite J C, Matlaga B, McCullough D et al. Transrectal ultrasound and biopsy in the early diagnosis of prostate cancer. Cancer Control 2000; 8(2): 141-150.
8. Tan C H, Wang J and Kundra V. Diffusion weighted imaging in prostate cancer. Eur Radiol 2011; 21(3): 593-603.
9. Reda I, Shalaby A, Khalifa F et al. Computer-aided diagnostic tool for early detection of prostate cancer. In IEEE international conference on image processing. Phoenix, Ariz., USA, Sep. 25-28 2016: IEEE, pp. 2668-2672.
10. Tamada T, Sone T, Jo Y et. al. Diffusion-weighted MRI and its role in prostate cancer. NMR Biomed 2014; 27(1): 25-38.
11. Viswanath S E, Bloch N B, Chappelow J C et al. Central gland and peripheral zone prostate tumors have significantly different quantitative imaging signatures on 3 tesla endorectal, in vivo T2-weighted M R imagery. J Magn Reson Imaging 2012; 36(1): 213-224.
12. Hambrock T, Vos P C, Hulsbergen-V D Kaa C A et al. Prostate cancer: computer-aided diagnosis with multiparametric 3-T MR imaging effect on observer performance. Radiology 2013; 266(2): 521-530.
13. Litjens G, Debats O, Barentsz J et al. Computer-aided detection of prostate cancer in MRI. IEEE Trans Med Imaging 2014; 33(5): 1083-1092.
14. Kwak J T, Xu S, Wood B J et al. Automated prostate cancer detection using T2-weighted and high-b-value diffusion-weighted magnetic resonance imaging. Med Phys 2015; 42(5): 2368-2378.
15. Peng Y, Jiang Y, Yang C et al. Quantitative analysis of multiparametric prostate M R images: differentiation between prostate cancer and normal tissue and correlation with gleason score-a computer-aided diagnosis development study. Radiology 2013; 267(3): 787-796.
16. Boesen L, Chabanova E, Løgager V et. al. Apparent diffusion coefficient ratio correlates significantly with prostate cancer gleason score at final pathology. J Magn Reson Imaging 2015; 42(2): 446-453.
17. McClure P, Khalifa F, Soliman A et al. A novel NMF guided level-set for DWI prostate segmentation. J Comput Sci Syst Biol 2014; 7(6): 209-216.
18. Le Bihan D. Apparent diffusion coefficient and beyond: what diffusion MR imaging can tell us about tissue structure. Radiology 2013; 268(2): 318-322.
19. Bengio Y, Lamblin P, Popovici D et al. Greedy layerwise training of deep networks. In Advances in neural information processing systems. Vancouver, BC, Canada, Dec. 4-7 2006, pp. 153-160.
20. Han J, Zhang D, Wen S et al. Two-stage learning to predict human eye fixations via SDAEs. IEEE Trans Cybern 2016; 46(2): 487-498.
21. Boureau Y I, Cun Y L et al. Sparse feature learning for deep belief networks. In Advances in neural information processing systems. Vancouver, BC, Canada, Dec. 3-6 2007, pp. 1185-1192.
22. Hosseini-Asl E, Zurada J M and Nasraoui O. Deep learning of part-based representation of data using sparse autoencoders with nonnegativity constraints. IEEE Trans Neural Networks Learn Syst 2016; 27(12): 2486-2498.
23. Bengio Y, Courville A and Vincent P. Representation learning: A review and new perspectives. IEEE Trans Pattern Anal Mach Intell 2013; 35(8): 1798-1828.
24. Yan K, Li C, Wang X et al. Comprehensive autoencoder for prostate recognition on MR images. In IEEE international symposium on biomedical imaging. Prague, Czech Republic, Apr. 13-16 2016: IEEE, pp. 1190-1194.
25. Rota Bulo S and Kontschieder P. Neural decision forests for semantic image labelling. In IEEE conference on computer vision and pattern recognition. Columbus, Ohio, USA, Jun. 24-27 2014, pp. 81-88.
26. Tsehay Y K, Lay N S, Roth H R et al. Convolutional neural network based deep-learning architecture for prostate cancer detection on multiparametric magnetic resonance images. In SPIE medical imaging. Orlando, Fla., USA, Feb. 11-16 2017, pp. 1013405-1013405.
27. Le M H, Chen J, Wang L et al. Automated diagnosis of prostate cancer in multi-parametric MRI based on multimodal convolutional neural networks. Phys Med Biol 2017; 62(16): 6497-6514.
28. Clark T, Wong A, Haider M A et al. Fully deep convolutional neural networks for segmentation of the prostate gland in diffusion-weighted MR images. In International conference image analysis and recognition. Montreal, Canada, Jul. 5-7 2017: Springer, pp. 97-104.
29. Chung A G, Shafiee M J, Kumar D et al. Discovery radiomics for multi-parametric MRI prostate cancer detection. arXiv preprint 2015; arXiv:1509.00111.
30. Liu S, Zheng H, Feng Y et al. Prostate cancer diagnosis using deep learning with 3D multiparametric MRI. arXiv preprint 2017; arXiv:1703.04078.
31. Hall M et al. The WEKA data mining software: an update. SIGKDD Explor Newsl 2009; 11(1): 10-18.
32. Skalska H and Freylich V. Web-bootstrap estimate of area under ROC curve. Austrian J Stat 2016; 35(2-3): 325-330.

What is claimed is:
1. A method for diagnosing prostate cancer comprising:
obtaining magnetic resonance imaging prostate data at a plurality of b-values;
processing the magnetic resonance imaging prostate data through a plurality of first autoencoders to create a plurality of imaging output probability data, wherein each of the plurality of first autoencoders processes the magnetic resonance imaging prostate data associated with only one of the plurality of b-values;
organizing the plurality of imaging output probability data into an input vector, wherein the input vector is a one-dimensional list of the imaging output probability data;
obtaining biological data from a biological value test, wherein the biological data is not the magnetic resonance imaging prostate data;

processing the biological data through a data classifier to create biological output probability data, wherein the input vector further includes the biological output probability data;

processing the input vector through a second autoencoder to generate a diagnostic probability of prostate cancer; and generating a diagnosis based on the diagnostic probability.

2. The method of claim 1, wherein the biological value test is based at least in part on a test selected from the group consisting of a digital rectal examination, a prostate specific antigen blood test, a needle biopsy, a patient questionnaire, or a histology-based test.

3. The method of claim 1, wherein the data classifier is based at least in part on a low-dimensional classifier selected from the group consisting of a K-nearest neighbor classifier or a softmax regression classifier.

4. The method of claim 1, wherein the plurality of first autoencoders and the second autoencoder are selected from the group consisting of a stacked non-negativity constrained sparse autoencoder, a non-negatively constrained sparse autoencoder, a softmax regression classifier, or a convolutional neural network.

5. The method of claim 1, wherein obtaining magnetic resonance imaging prostate data comprises:
   determining an intensity-based imaging feature from a magnetic resonance imaging scan;
   creating a plurality of intensity-based feature maps from magnetic resonance imaging data based on the plurality of b-values, wherein each of the plurality of intensity-based feature maps is associated with only one of the plurality of b-values; and
   generating magnetic resonance imaging prostate data by applying the plurality of intensity-based feature maps to a plurality of cumulative distribution functions based on the plurality of b-values, wherein each of the plurality of cumulative distribution functions is associated with only one of the plurality of b-values.

6. The method of claim 5, wherein the magnetic resonance imaging scan is a diffusion-weighted magnetic resonance imaging scan.

7. The method of claim 5, wherein the intensity-based imaging feature is an apparent diffusion coefficient.

8. The method of claim 1, wherein the plurality of b-values are selected from the range of about 0 s/mm$^2$ to about 700 s/mm$^2$.

9. A system, comprising:
one or more processors; and
memory containing program code that, when executed by at least one of the one or more processors, is configured to:
   process magnetic resonance imaging prostate data through a plurality of first autoencoders to create a plurality of imaging output probability data, wherein each of the plurality of first autoencoders processes the magnetic resonance imaging prostate data associated with only one of a plurality of b-values;
   organize the plurality of imaging output probability data into an input vector, wherein the input vector is a one-dimensional list of the imaging output probability data;
   process biological data through a data classifier, wherein the biological data is not the magnetic resonance imaging prostate data, and wherein the input vector further includes the biological output probability data;
   process the input vector through a second autoencoder to generate a diagnostic probability of prostate cancer; and
   generate a diagnosis based on the diagnostic probability.

10. The system of claim 9, wherein the data classifier is based at least in part on a low-dimensional classifier selected from the group consisting of a K-nearest neighbor classifier or a softmax regression classifier.

11. The system of claim 9, wherein the plurality of first autoencoders and the second autoencoder are selected from the group consisting of a stacked non-negativity constrained sparse autoencoder, a non-negatively constrained sparse autoencoder, a softmax regression classifier, or a convolutional neural network.

12. The system of claim 9, wherein obtaining magnetic resonance imaging prostate data further causes the system to:
   determine an intensity-based imaging feature from a magnetic resonance imaging scan;
   create a plurality of intensity-based feature maps from magnetic resonance imaging data based on the plurality of b-values, wherein each of the plurality of intensity-based feature maps is associated with only one of the plurality of b-values; and
   generate magnetic resonance imaging prostate data by applying the plurality of intensity-based feature maps to a plurality of cumulative distribution functions based on the plurality of b-values, wherein each of the plurality of cumulative distribution functions is associated with only one of the plurality of b-values.

13. The system of claim 12, wherein the magnetic resonance imaging scan is a diffusion-weighted magnetic resonance imaging scan.

14. The system of claim 12, wherein the intensity-based imaging feature is an apparent diffusion coefficient.

15. The system of claim 9, wherein the plurality of b-values are selected from the range of about 0 s/mm$^2$ to about 700 s/mm$^2$.

* * * * *